United States Patent
Litvak et al.

(10) Patent No.: US 7,702,396 B2
(45) Date of Patent: Apr. 20, 2010

(54) OPTIMIZING PITCH ALLOCATION IN A COCHLEAR IMPLANT

(75) Inventors: Leonid M. Litvak, Los Angeles, CA (US); Lakshmi N. Mishra, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 1195 days.

(21) Appl. No.: 10/992,625

(22) Filed: Nov. 17, 2004

(65) Prior Publication Data

US 2005/0137651 A1    Jun. 23, 2005

Related U.S. Application Data

(60) Provisional application No. 60/523,928, filed on Nov. 21, 2003.

(51) Int. Cl.
*A61N 1/00* (2006.01)
(52) U.S. Cl. .................................................. 607/57
(58) Field of Classification Search ............ 607/55–57; 707/6
See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,495,384 A | 1/1985 | Scott et al. | |
| 4,793,353 A | 12/1988 | Borkan | 607/60 |
| 4,819,647 A | 4/1989 | Byers et al. | |
| 5,603,726 A | 2/1997 | Schulman et al. | |
| 5,626,629 A | 5/1997 | Faltys et al. | |
| 5,938,691 A | 8/1999 | Schulman et al. | |
| 6,026,400 A * | 2/2000 | Suzuki | 707/6 |
| 6,052,624 A | 4/2000 | Mann | |
| 6,067,474 A | 5/2000 | Schulman et al. | |

(Continued)

FOREIGN PATENT DOCUMENTS

WO          00/01200          1/2000

(Continued)

OTHER PUBLICATIONS

Harnsberger, et al., "Perceptual 'vowel spaces' of Cochlear Implant Users: Implications for the Study of Auditory Adaptation to Spectral Shift", J Acoust Soc Am, vol. 109(5) pt. 1, (May 2001), pp. 2135-2145.

(Continued)

*Primary Examiner*—George Manuel
(74) *Attorney, Agent, or Firm*—Wong, Cabello, Lutsch, Rutherford & Brucculeri LLP

(57) ABSTRACT

Errors in pitch allocation within a cochlear implant are corrected in order to provide a significant and profound improvement in the quality of sound perceived by the cochlear implant user. The disclosure provides a tool for determining the implant fitting curve for cochlear implant system to correct pitch warping. The method presents familiar musical tunes to determine the implant fitting slope (relative alignment). In addition, in one embodiment, speech sounds may be used to determine the offset of the fitting line (absolute alignment). The use of music and speech to determine the implant fitting curve (line) and the slope is facilitated by using techniques to implement virtual electrodes to more precisely direct stimuli to the location or "place" on the cochlea.

31 Claims, 18 Drawing Sheets

U.S. PATENT DOCUMENTS

| | | | |
|---|---|---|---|
| 6,078,838 A | 6/2000 | Rubinstein | |
| 6,129,753 A | 10/2000 | Kuzma | |
| 6,154,678 A | 11/2000 | Lauro | 607/115 |
| 6,157,861 A | 12/2000 | Faltys et al. | |
| 6,181,969 B1 | 1/2001 | Gord | |
| 6,195,585 B1 | 2/2001 | Karunasiri et al. | |
| 6,205,360 B1 | 3/2001 | Carter et al. | |
| 6,208,882 B1 | 3/2001 | Lenarz et al. | |
| 6,216,045 B1 | 4/2001 | Black et al. | 607/122 |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,295,467 B1 | 9/2001 | Kollmeier et al. | |
| 6,393,325 B1 | 5/2002 | Mann et al. | |
| 6,415,185 B1 | 7/2002 | Maltan | |
| 6,516,227 B1 | 2/2003 | Meadows et al. | |
| 6,915,166 B1 * | 7/2005 | Stecker et al. | 607/55 |
| 7,200,504 B1 | 4/2007 | Fister | |
| 7,203,548 B2 | 4/2007 | Whitehurst et al. | |
| 7,242,985 B1 | 7/2007 | Fridman et al. | |
| 7,251,530 B1 | 7/2007 | Overstreet et al. | |
| 7,277,760 B1 | 10/2007 | Litvak et al. | |
| 7,292,890 B2 | 11/2007 | Whitehurst et al. | |
| 7,292,892 B2 | 11/2007 | Litvak et al. | |
| 7,308,303 B2 | 12/2007 | Whitehurst et al. | |
| 7,376,466 B2 | 5/2008 | He et al. | |
| 7,444,180 B2 | 10/2008 | Kuzma et al. | |
| 7,445,528 B1 | 11/2008 | Kuzma | |
| 7,450,994 B1 | 11/2008 | Mishra et al. | |
| 7,522,961 B2 | 4/2009 | Fridman et al. | |
| 7,599,500 B1 | 10/2009 | Segel et al. | |
| 7,627,383 B2 | 12/2009 | Haller et al. | |
| 2003/0036782 A1 | 2/2003 | Hartley et al. | 607/57 |
| 2003/0114905 A1 | 6/2003 | Kuzma | |
| 2004/0015204 A1 | 1/2004 | Whitehurst et al. | |
| 2004/0015205 A1 | 1/2004 | Whitehurst et al. | |
| 2005/0137651 A1 | 6/2005 | Litvak et al. | |
| 2005/0209652 A1 | 9/2005 | Whitehurst | |
| 2005/0240229 A1 | 10/2005 | Whitehurst | |
| 2005/0267555 A1 | 12/2005 | Marnfeldt | |
| 2006/0100672 A1 | 5/2006 | Litvak | |
| 2006/0161204 A1 | 7/2006 | Colvin et al. | |
| 2006/0167521 A1 | 7/2006 | He et al. | |
| 2006/0184204 A1 | 8/2006 | He | |
| 2006/0195143 A1 | 8/2006 | McClure | |
| 2006/0229688 A1 | 10/2006 | McClure et al. | |
| 2006/0271109 A1 | 11/2006 | Kuzma | |
| 2007/0021800 A1 | 1/2007 | Whitehurst et al. | |
| 2007/0049988 A1 | 3/2007 | Carbunaru | |
| 2007/0055308 A1 | 3/2007 | Haller et al. | |
| 2007/0066997 A1 | 3/2007 | He | |
| 2007/0112403 A1 | 5/2007 | Moffitt | |
| 2007/0112404 A1 | 5/2007 | Mann | |
| 2007/0123938 A1 | 5/2007 | Haller et al. | |
| 2007/0219595 A1 | 9/2007 | He | |
| 2007/0260292 A1 | 11/2007 | Faltys et al. | |
| 2007/0293785 A1 | 12/2007 | Litvak | |
| 2008/0085023 A1 | 4/2008 | Kulkarni | |
| 2008/0132961 A1 | 6/2008 | Jaax | |

FOREIGN PATENT DOCUMENTS

| | | |
|---|---|---|
| WO | 02/09808 | 2/2002 |
| WO | 03/015863 | 2/2003 |
| WO | 2004/043537 | 5/2004 |
| WO | 2006/053101 | 5/2006 |
| WO | 2007/030496 | 3/2007 |
| WO | 2007/059343 | 5/2007 |
| WO | 2007/130782 | 11/2007 |

OTHER PUBLICATIONS

McDermott, et al., "Pitch Ranking with Nonsimultaneous Dual-Electrode Electrical Stimulation of the Cochlea", J Acoust Soc Am, vol. 96(1), (1994) pp. 155-162.

Morse, et al., "The practical Use of Noise to Improve Speech Coding by Analogue Cochlear Implants", Chaos, Solutions and Fractals, vol. 11, No. 12, (2000) pp. 1885-1894.

Rubinstein et al., "The Neurophysiological Effects of Simulated Auditory Prosthesis Simulation" Second Quarterly Progress Report NO1-DC-6-2111.

Scheirer, et al., "Construction and Evaluation of Robust Multifeature Speech/Music Discriminator", Acoustics, Speech, and Signal Processing (1997), IEEE International Conference on Munich, Germany (Apr. 21-24, 1997), pp. 1331-1334.

Smith, et al., "Chimaeric Sounds, Reveal Dichotomies in Auditory Perception", Nature, vol. 416, No. 6876, (Mar. 7, 2002), pp. 87-90.

van Wieringen, et al., "Comparison of Procedures to Determine Electrical Stimulation Thresholds in Cochlear Implant Users", Ear and Hearing, vol. 22(6), (2001), pp. 528-538.

Zeng, et al., "Loudness of Simple and Complex Stimuli in Electric Hearing", Annals of Otology, Rhinology & Laryngology, vol. 104 (9), (1995) pp. 235-238.

Zhang, et al., "Loudness of Dynamic Stimuli in Acoustic and Electric Hearing", J Acoust Soc Am, vol. 102(5) Pt. 1, (Nov. 1997), pp. 2925-2934.

U.S. Appl. No. 10/188,465, Kuzma, filed Jul. 2, 2002.
U.S. Appl. No. 11/089,171, Hahn, filed Mar. 24, 2005.
U.S. Appl. No. 11/122,648, Griffith, filed May 5, 2005.
U.S. Appl. No. 11/139,296, Carbunaru, filed May 26, 2005.
U.S. Appl. No. 11/178,054, Faltys, filed Jul. 8, 2005.
U.S. Appl. No. 11/226,777, Faltys, filed Sep. 13, 2005.
U.S. Appl. No. 11/261,432, Mann, filed Oct. 28, 2005.
U.S. Appl. No. 11/262,055, Fridman, filed Dec. 28, 2005.
U.S. Appl. No. 11/386,198, Saoji, filed Mar. 21, 2006.
U.S. Appl. No. 11/387,206, Harrison, filed Mar. 23, 2006.
U.S. Appl. No. 11/534,933, Faltys, Sep. 25, 2006.
U.S. Appl. No. 11/765,395, Fridman et al., filed Jun. 19, 2007.
U.S. Appl. No. 60/433,037, Overstreet, filed Dec. 11, 2002.
U.S. Appl. No. 60/523,928, Litvak, filed Nov. 21, 2003.
U.S. Appl. No. 60/665,171, Harrison, filed Mar. 24, 2005.
U.S. Appl. No. 60/669,822, McClure, filed Apr. 5, 2005.
U.S. Appl. No. 60/950,324, Fridman et al., filed Jul. 17, 2007.
U.S. Appl. No. 60/975,111, Kulkarni et al., filed Sep. 25, 2007.

* cited by examiner

OPTIMIZING PITCH ALLOCATION IN A COCHLEAR IMPLANT

RELATED APPLICATIONS

The present application claims the benefit of priority of U.S. Provisional Patent Application Ser. No. 60/523,928, entitled "Optimizing Pitch Allocation in a Cochlear Implant Using Simple Melodies", filed Nov. 21, 2003, which provisional application is hereby incorporated by reference in its entirety.

TECHNICAL FIELD

The present disclosure relates to implantable neurostimulator systems, such as cochlear implants and, more particularly, to a method for optimizing pitch allocation as implemented in a cochlear implant.

BACKGROUND

Prior to the past several decades, scientists generally believed that it was impossible to restore hearing to the deaf. However, scientists have had increasing success in restoring normal hearing to the deaf through electrical stimulation of the auditory nerve. The initial attempts to restore hearing were not very successful, as patients were unable to understand speech. However, as scientists developed different techniques for delivering electrical stimuli to the auditory nerve, the auditory sensations elicited by electrical stimulation gradually came closer to sounding more like normal speech. The electrical stimulation is implemented through a prosthetic device, called cochlear implant, that is implanted in the inner ear to restore partial hearing to profoundly deaf people.

At present, very few cochlear implant patients are able to enjoy music. This is due, in part, to the fact that the cochlear fitting programs that process delivery of certain sound frequencies through a selected electrode or electrodes do not compensate for errors in pitch allocation.

Within the cochlea, there are two main cues that convey "pitch" (frequency) information to the patient. They are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to the basilar direction.

Mapping an electrode array in a cochlear duct to the correct audio frequencies is complicated by differences in an individual's anatomy. In addition, the final implanted position of the electrode array tends to be variable, which lends an arbitrariness to a mapping scheme between an electrode contact and perceived sound frequency. Thus, an optimal fitting map between an electrode contact and a sound frequency can only be roughly estimated at the outset for each individual. The initial estimate typically is inaccurate for that individual.

Another complicating factor is that the position of each electrode is not very precise, i.e., there are only a limited number of electrodes, e.g., numbering about 16 to 24 electrodes, spread along the length of the electrode array, inserted into one of the spiraling ducts of the cochlea. Hence, mapping to a "place" within the cochlea is not precise and is limited by the resolution of the discretely placed electrodes.

SUMMARY

The present inventors recognized that an improved fitting tool was needed to better convey pitch information to a user of a cochlear implant. The disclosed devices and methods address this need by providing a fitting routine for determining the fitting line and slope of a cochlear implant and electrode array. The disclosed devices and methods further provide a tool for quickly and accurately correcting pitch allocation errors in fitting cochlear implants. The result permits the significant improvement in the perception of sounds so that patients may enjoy music and more accurately perceive sounds having characteristic pitch information such as speech.

In some embodiments, the fitting tool takes advantage of the concept of "virtual electrodes" which permits stimulation to be directed more precisely to a "place" on the cochlea, which place may be between electrodes. Such "in-between" stimulation is not feasible in a conventional cochlear system. The use of virtual electrodes allows directed stimulation to nearly an infinite number of places on the cochlea. One example for implementing virtual electrodes is by using weighted current steering through two or more electrodes. Another example for implementing virtual electrodes is by applying stimuli at two closely placed electrodes in an alternating, time-multiplexed manner, so that stimuli are presented at the two electrodes non-simultaneously.

In one aspect, fitting a cochlear implant system includes implanting a multi-electrode array into the cochlea of a user, the multi-electrode array having an associated implant fitting line that defines a relationship between cochlear places of implant electrodes and associated audio frequencies; presenting variations of a musical melody to the user through the multi-electrode array; allowing the user to select a variation of the musical melody that most closely conforms to a musical melody as remembered by the user; and determining a correct slope of the implant fitting line of the multi-electrode array based on the rendition of the musical melody selected by the user.

In another aspect, fitting a cochlear implant system includes fitting a cochlear implant system is provided. The method comprises: (a) implanting a multi-electrode array into the cochlea of a user; (b) determining a best slope of an implant fitting line by repetitively presenting a musical tune to the user, while varying the slope of the implant fitting line, through the multi-electrode array, wherein the implant fitting line defines a relationship between cochlear places of implant electrodes and associated audio frequencies; (c) allowing the user to select a tune with a particular implant fitting line slope that is most like the tune as remembered by the user; and (d) determining an offset of the implant fitting line relative to an intrinsic fitting line of the user's cochlea by repetitively presenting a familiar sound to the user, while varying the offset of the implant fitting line, through the multi-electrode array, and allowing the user to select a familiar sound with a particular offset, such that the familiar sound with the particular offset is most like the sound with the pitch as remembered, wherein virtual electrodes are implemented to precisely deliver stimuli to places on the cochlea while delivering tunes or sounds to the user.

In another aspect, finding the slope of an implant fitting line includes: (a) implanting a multi-electrode array into the cochlea of a user; and (b) determining the slope of an implant fitting line by repetitively presenting a musical tune to the user, but with different slopes at each presentation, through the multi-electrode array and allowing the user to select a tune with a particular slope that is most like the tune as remembered, wherein the implant fitting line defines a relationship between cochlear places of implant electrodes and associated audio frequencies, wherein virtual electrodes are implemented to precisely deliver stimuli to places on the cochlea while delivering tunes to the user.

In another aspect, a cochlear implant includes: an implantable pulse generator; an electrode array having a multiplicity of electrodes connected to the implantable pulse generator; means for generating a musical tune delivered through the electrode array with different slopes; and means for implementing virtual electrodes.

In another aspect, fitting a cochlear implant system includes: (a) implanting a multi-electrode array into the cochlea of a user; (b) presenting a first musical melody to a user through the multi-electrode array, the first musical melody comprising a series of notes, each note having a predetermined frequency and duration; (c) varying the frequency of one or more of the notes of the first melody in a predetermined manner to present a second musical melody to the user, the second musical melody being a distorted version of the first musical melody, wherein the user perceives that the second musical melody conforms to a musical melody remembered by the user; and (d) adjusting an implant fitting line of the multi-electrode array based on the variation between the first musical melody and the second musical melody, wherein the implant fitting line defines a relationship between cochlear places of implant electrodes and associated audio frequencies.

In another aspect, fitting a cochlear implant system includes: implanting a multi-electrode array into a cochlea of a user, the electrodes being positioned on the array to have a spatial relationship with associated audio frequencies corresponding to positions along the user's cochlea; presenting two or more variations of a sound to the user through the multi-electrode array; allowing the user to select a desired variation of the sound; and, based on the variation selected by the user, determining a correct fitting of the multi-electrode array relative to the user's cochlea The described methods and systems are suited for users of cochlear implants who have past experience in hearing simple, musical tunes and remember such tunes. A disclosed feature is to provide a fitting tool that can be used in patients who do not have formal musical training. Another feature is to provide a fitting tool that can be implemented with a software program and that can be accomplished quickly and accurately in a clinical setting.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

The following description is of the best mode presently contemplated for carrying out the disclosed devices and methods. This description is not to be taken in a limiting sense, but is made merely for the purpose of describing the general principles of the disclosed systems and methods. The scope of the described systems and methods should be determined with reference to the claims.

The present disclosure describes a tool to better determine the implant fitting curve (line) for a cochlear implant. Simple musical melodies are used to help properly map specific electrodes and/or "places" on the cochlea to corresponding perceived audio frequencies. This mapping can be referred to as an "implant fitting curve (line)" and depends in particular on the type of electrode array used, the type of cochlear implant, and the individual's anatomical variation. When the implant fitting line is properly determined and implemented in a cochlear implant system, the patient is able to experience a significant improvement in the perceived quality of sound, particularly with music and speech.

The present methods and devices sometimes use the concept of virtual electrodes to deliver better quality sound by more accurately directing stimulation current to the location or "place" on a cochlea which precisely corresponds to the audio sound frequency that the stimulation is intended to convey. Stimulation currents can be more precisely directed by employing the concept of virtual electrodes, such that the resulting perception appears to arise from the presence of a virtual electrode located somewhere between two physical electrodes. One way to achieve virtual electrodes is by providing concurrent, weighted currents at two electrodes. "Current steering" is thus achieved. Another technique for achieving a virtual electrode is to rapidly and alternately stimulate two closely placed electrodes, referred to hereinafter as a "time-multiplexed", non-simultaneous, presentation of stimuli to implement a virtual electrode. Employment of such techniques to achieve virtual electrodes, allows stimulus current to be directed to an almost unlimited number of locations or "places" within the cochlea.

It will be helpful first to provide an overview of the structure of a cochlear implant system. Such overview is provided below in connection with the description of FIGS. 1, 2A and 2B.

Figure 1:
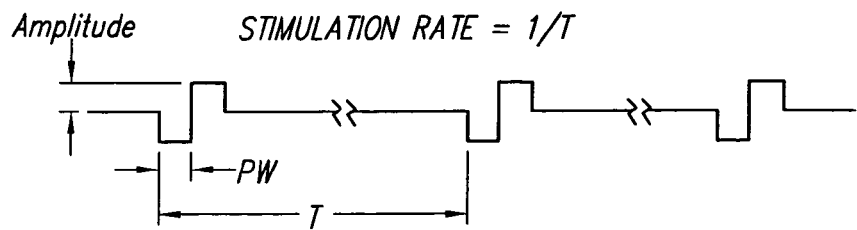
FIG. 1 is a current stimulation waveform that defines the stimulation rate (1/T) and biphasic pulse width (PW) associated with electrical stimuli, as those terms are commonly used in the neurostimulation art.

FIG. 1 shows a waveform diagram of a biphasic pulse train. The waveform shown defines stimulation rate (1/T), pulse width (PW) and pulse amplitude as those terms are commonly used in connection with a neurostimulator device, such as a cochlear implant, a spinal cord stimulator (SCS), a deep brain stimulator (DBS) or other neural stimulator. All such systems commonly generate biphasic pulses of the type shown in FIG. 1 in order to produce a desired therapeutic effect.

A "biphasic" pulse generally consists of two pulses: a first pulse of one polarity having a specified magnitude, followed immediately or after a very short delay, by a second pulse of the opposite polarity having the same total charge, which charge is the product of stimulus current multiplied by the duration of each pulse or phase. It is believed that "charge balancing" can prevent tissue damage at the site of stimulation and prevent electrode corrosion.

Figure 2A:
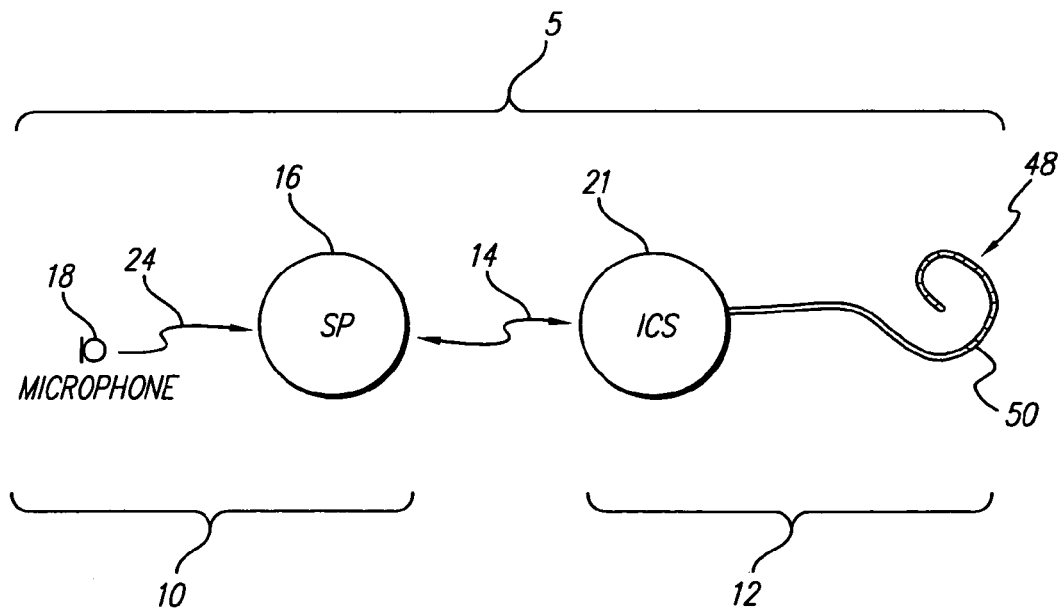
FIGS. 2A and 2B, respectively, show a cochlear implant system and a partial functional block diagram of the cochlear stimulation system, which system is capable of providing high rate pulsatile electrical stimuli and virtual electrodes.

FIG. 2A shows an example cochlear stimulation system that may be used. The system includes a speech processor portion 10 and a cochlear stimulation portion 12. The speech processor portion 10 includes a speech processor (SP) 16 and a microphone 18. The microphone 18 may be connected directly to the SP 16 or may be coupled to the SP 16 through an appropriate communication link 24. The cochlear stimulation portion 12 includes an implantable cochlear stimulator (ICS) 21 and an electrode array 48. The electrode array 48 is adapted to be inserted within a duct of the cochlea. The array 48 includes a multiplicity of electrodes 50, e.g., sixteen electrodes, spaced along its length that are selectively connected to the ICS 21. The electrode array 48 may be substantially as shown and described in U.S. Pat. Nos. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as linked together electronically through a suitable data or communications link 14. In some cochlear implant systems, the SP 16 and microphone 18 comprise the external portion of the cochlear implant system and the ICS 21 and electrode array 48 comprise the implantable portion of the system. Thus, the data link 14 is a transcutaneous (through the skin) data link that allows power and control signals to be sent from the SP16 to the ICS 21. In some embodiments, data and status signals may also be sent from the ICS 21 to the SP 16.

Figure 2B:
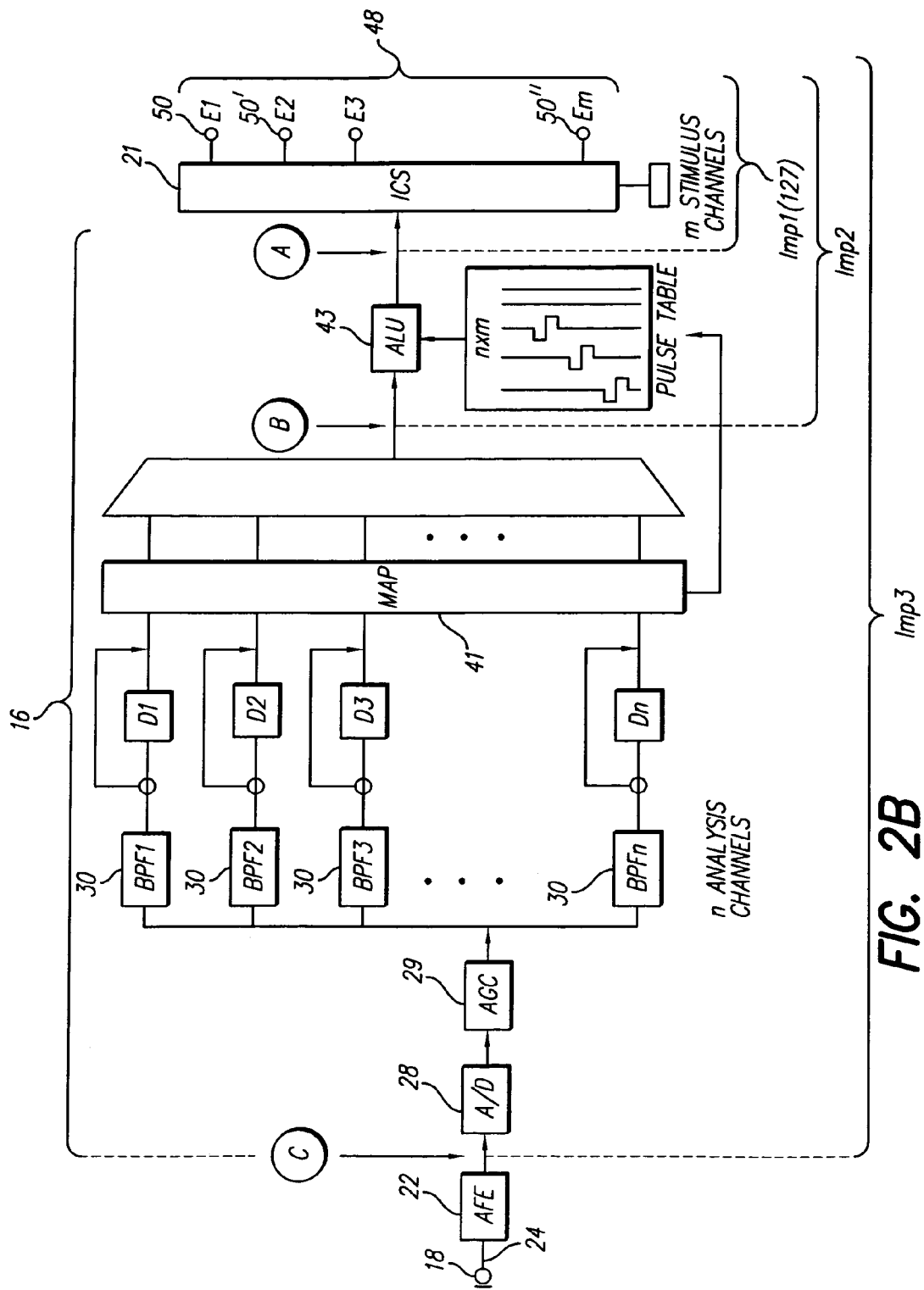

In a conventional cochlear implant system, as shown more particularly in FIG. 2B, at least certain portions of the SP 16 are included within the implantable portion of the overall cochlear implant system, while other portions of the SP 16 remain in the external portion of the system. In general, at least the microphone 18 and associated analog front end (AFE) circuitry 22 will be part of the external portion of the system and at least the ICS 21 and electrode array 48 are part of the implantable portion. As used herein, "external" means not implanted under the skin or residing within the inner ear. However, "external" can also mean within the outer ear, including in the ear canal or can include residing within the middle ear.

Typically, where a transcutaneous data link must be established between the external portion and the implantable portions of the system, such link is realized by an internal antenna coil within the implantable portion and an external antenna coil within the external portion. In use, the external antenna coil is aligned over the location where the internal antenna coil is implanted, allowing such coils to be inductively coupled to each other, thereby allowing data, e.g., the magnitude and polarity of a sensed acoustic signals and power to be transmitted from the external portion to the implantable portion. Note, in other embodiments, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals and may thus be considered an acoustic transducer. The electrical signals are sent to the SP 16 over a suitable electrical or other link 24. The SP 16 processes these converted acoustic signals in accordance with a selected speech processing strategy to generate appropriate control signals for controlling the ICS 21. Such control signals specify or define the polarity, magnitude, location (which electrode pair or electrode group receive the stimulation current), and timing (when the stimulation current is applied to the electrode pair) of the stimulation current that is generated by the ICS. Such control signals thus combine to produce a desired spatio-temporal pattern of electrical stimuli in accordance with the desired speech processing strategy. Unlike earlier cochlear implant systems, more recent cochlear implant systems advantageously confine such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes 50 of the electrode array 48. Such speech processing strategy involves defining a pattern of stimulation waveforms that are to be applied to the electrodes as controlled electrical currents.

Analog waveforms used in analog stimulation patterns are typically reconstructed by the generation of continuous, short monophasic pulses (samples). The sampling rate is selected to be fast enough to allow for proper reconstruction of the temporal details of the signal. An example of such a sampled analog stimulation pattern is a simultaneous analog sampler (SAS) strategy.

Turning next to FIG. 2B, a partial block diagram of a representative cochlear implant that may be used to implement the present methods and devices is shown. More particularly, FIG. 2B shows a partial functional block diagram of the SP 16 and the ICS 21 of an exemplary cochlear implant system capable of providing a high rate pulsatile stimulation pattern and virtual electrodes. FIG. 2B depicts the functions that are carried out by the SP 16 and the ICS 21. It should also be pointed out that the particular functions shown in FIG. 2B (dividing the incoming signal into frequency bands and independently processes each band) are representative of just one type of signal processing strategy that may be employed. Other signal processing strategies could just as easily be used to process the incoming acoustical signal. The devices and methods described herein could still be used to provide added flexibility in specifying the stimulation patterns and waveforms that are selected and used with such additional signal processing strategies.

A complete description of the functional block diagram of the cochlear implant shown in FIG. 2B is found in U.S. Pat. No. 6,219,580 ('580 patent), incorporated herein by reference. It is emphasized that the cochlear implant functionality shown in FIG. 2B is only representative of one type of cochlear implant and is not intended to be limiting.

In the manner described in the '580 patent, the cochlear implant functionally shown in FIG. 2B provides n analysis channels that may be mapped to one or more stimulus channels. That is, as seen in FIG. 2B, after the incoming sound signal is received through the microphone 18 and the analog front end circuitry (AFE) 22, it is digitized in an analog to digital (A/D) converter 28 and then subjected to appropriate gain control (which may include compression) in an automatic gain control (AGC) unit 29. After appropriate gain control, the signal is divided into n analysis channels, each of which includes a bandpass filter, BPFn, centered at a selected frequency. The signal present in each analysis channel is processed as described more fully in the '580 patent or as is appropriate using other signal processing techniques and the signals from each analysis channel are then mapped, using mapping function 41, so that an appropriate stimulus current of a desired amplitude and timing, may be applied through a selected stimulus channel to stimulate the auditory nerve.

Two or more stimulus channels may be selected simultaneously with the stimulus current being dynamically weighted in an appropriate manner between the two or more channels to effectively steer the current from one stimulus location within the cochlea to another. The concept of current steering is taught in U.S. Pat. No. 6,393,325 ('325 patent), incorporated herein by reference, for use within a spinal cord stimulation system. However, current steering as taught in the '325 patent, may be employed within any type of neural stimulation system, including a cochlear implant system. Additional features and advantages of current steering are taught in International Publication Number WO 02/09808 A1, based on International Application Number PCT/US00/20294, filed 26 Jul. 2000, also incorporated herein by reference.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the user by the ICS 21 and its associated electrode array 48.

The electrode array 48 includes a multiplicity of electrode contacts 50, connected through appropriate conductors to respective current generators or pulse generators within the ICS. Through these multiplicity of electrode contacts, a multiplicity of stimulus channels, e.g., m stimulus channels, exist through which individual electrical stimuli may be applied at m different stimulation sites within the patient's cochlea or other tissue stimulation site.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Instead, in some instances, a different mapping scheme may prove beneficial to the patient.

For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites.

The "in-between" site at which a stimulus is applied may be referred to as a "stimulation site" produced by a virtual electrode. Advantageously, this capability of using different mapping schemes between n SP analysis channels and m ICS stimulation channels to thereby produce a large number of virtual and other stimulation sites provides a great deal of flexibility with respect to positioning the neural excitation areas precisely in the cochlear place that best conveys the frequencies of the incoming sound.

As explained in more detail below in connection with FIGS. 3A and 3B, through appropriate weighting and sharing of currents between two or more physical electrodes, it is possible to provide a large number of virtual electrodes between physical electrodes, thereby effectively steering the location at which a stimulus is applied to almost any location along the length of the electrode array.

The output stage of the ICS 21 which connects with each electrode E1, E2, E3, . . . Em of the electrode array may be as described in U.S. Pat. No. 6,181,969, incorporated herein by reference. Such output stage advantageously provides a programmable N-DAC or P-DAC (where DAC stands for digital-to-analog converter) connected to each electrode so that a programmed current may be sourced to the electrode or sunk from the electrode. Such configuration allows any electrode to be paired with any other electrode and the amplitudes of the currents can be programmed and controlled to gradually shift the stimulating current that flows from one electrode through the tissue to another adjacent electrode or electrodes, thereby providing the effect of "shifting" the current from one or more electrodes to another electrode(s). Through such current shifting, the stimulus current may be shifted or directed so that it appears to the tissue that the current is coming from or going to an almost infinite number of locations.

Still with reference to FIG. 2B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21 and its associated electrode array were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern cochlear implant, such as the CII Cochlear implant system manufactured by Advanced Bionics® Corporation of Sylmar, Calif., advantageously puts at least a portion of the speech processor 16 within the implanted portion of the system. For example, a cochlear implant may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with such a cochlear implant.

Future generations of cochlear implant systems may incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), would need only have a rate commensurate with the input acoustic signal.

Additional features made possible by the cochlear implant system shown in FIG. 2B or equivalents thereof and, which may be used in conjunction with the presently described devices and methods, allow the current stimuli to be applied to the target tissue at fast rates and in a way that more naturally elicits a stochastic firing of the target tissue, as taught, e.g., in U.S. patent application Ser. No. 10/218,645 (filed Aug. 13, 2002); 10/218,616 (filed: Aug. 13, 2002); and 60/425,215 (filed Nov. 8, 2002); and in International Patent Application Serial No. PCT/US01/25861 (filed Aug. 17, 2002), all of which applications are assigned to the same assignee as is the present application and all of which applications are incorporated herein by reference.

Figure 3A:
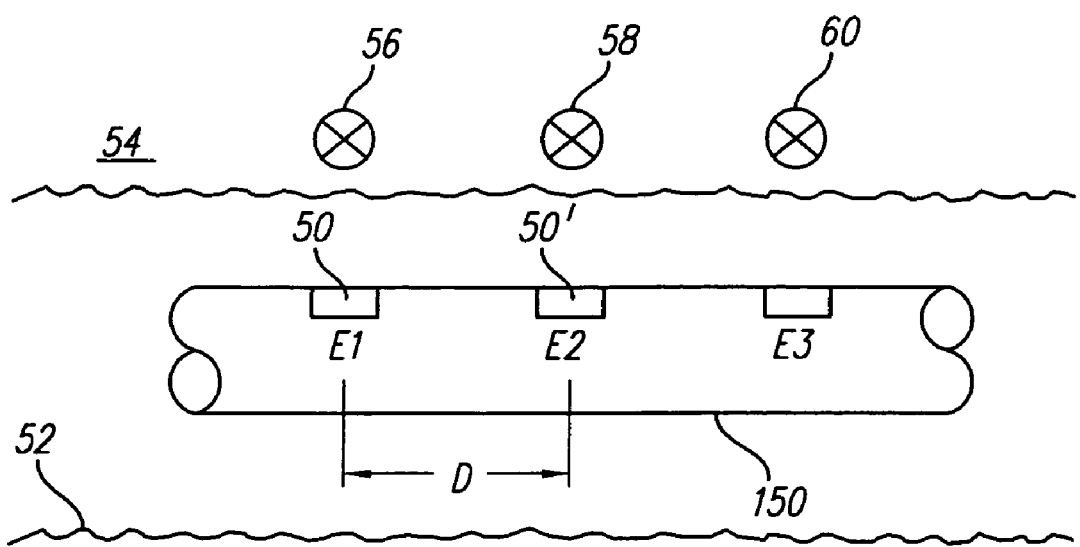
FIG. 3A schematically illustrates the locations of applied stimuli within a duct of the cochlea, without the benefit of virtual electrodes.

Next, with reference to FIG. 3A, a diagram is presented to illustrate the location where a stimulus is applied when virtual electrodes are employed. In FIG. 3A, three electrodes E1, E2 and E3 of an electrode array are illustrated. A reference electrode, not shown, is also presumed to be present some distance from the electrodes E1, E2 and E3, thereby allowing monopolar stimulation to occur between a selected one of the electrodes and the reference electrode. Bipolar stimulation could likewise occur, e.g., between electrodes E1 and E2, between E2 and E3, or between any other pair of electrodes.

The electrodes E1, E2 and E3 are located "in line" on a carrier 150, and are spaced apart from each other by a distance "D". Each electrode is electrically connected to a wire conductor (not shown) that is embedded within the carrier 150 and which connects the electrode to the ICS 21 (see FIG. 2A or 2B). The carrier 150 is shown inserted into a duct 52 within tissue 54 that is to be stimulated. For a cochlear implant system, the duct 52 typically comprises the scala tympani of a human cochlea.

When a stimulus current is applied to electrode E1, the stimulus location in the tissue 54 is essentially the location 56, adjacent the physical location of the electrode E1. Similarly, when a stimulus current is applied to electrode E2, the stimulus location in the tissue 54 is essentially the location 58, adjacent the physical location of the electrode E2. Likewise, when a stimulus current is applied to electrode E3, the stimulus location in the tissue 54 is essentially the location 60, adjacent the physical location of the electrode E3. It is thus seen that the resolution or precision, with which a stimulus may be applied to the tissue is only as good as is the spacing of the electrodes on the electrode array. That is, each stimulus location in the tissue 54 is separated by approximately the same distance "D" as separates the electrodes.

Figure 3B:
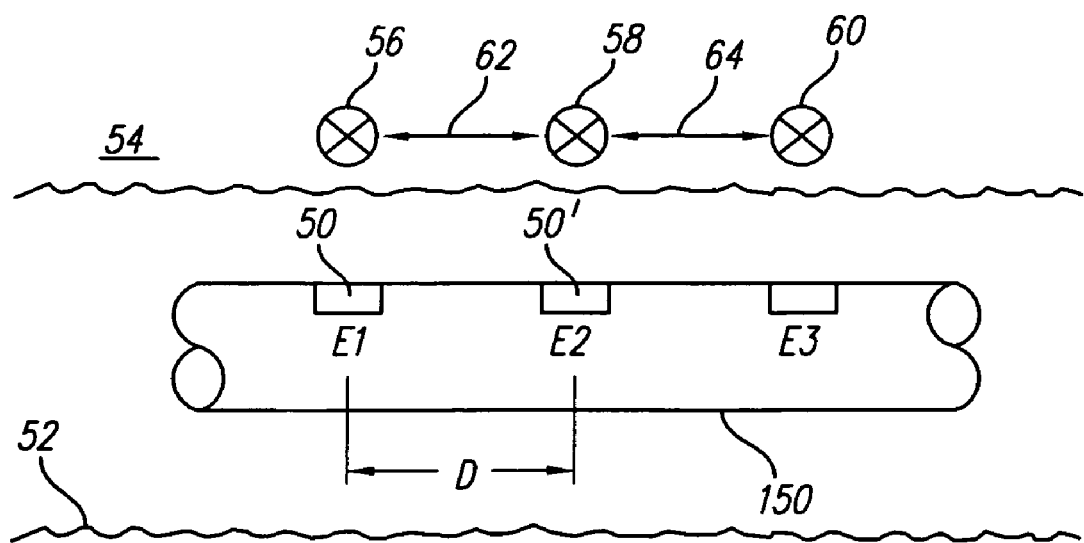
FIG. 3B schematically illustrates the locations of applied stimuli within a duct of the cochlea or other implanted location, with the benefit of virtual electrodes.

With reference to FIG. 3B, a diagram is presented to illustrate the location where a stimulus is applied when virtual electrodes are employed, specifically by using current steering. The structure of the electrode array and spacing between electrodes E1, E2 and E3 is the same as in FIG. 3A. Thus, when a stimulus current is applied only to electrode E1, the stimulus location in the tissue 54 is the location 56, the same as was the case in FIG. 3A. Similarly, when a stimulus current is applied only to electrode E2, the stimulus location in the tissue 54 is the location 58. Likewise, when a stimulus current is applied only to electrode E3, a stimulus location in the tissue 54 is the location 60. However, through application of current steering, a stimulus current may be shared, e.g., between electrodes E1 and E2 (and some other paired or reference electrode), and the effective tissue location where the stimulus is directed may be anywhere along the line 62 between points 56 and 58. Alternatively, if the current is shared between electrodes E2 and E3, the location in the tissue where the stimulus is directed may be anywhere along the line 64 between points 58 and 60.

To illustrate further, suppose a stimulus current having an amplitude I1 is applied to the tissue through electrode E1 (and some reference electrode). The location within the tissue 54 where the stimulus would be felt would be the point 56. However, if a stimulus current of only 0.9xI1 were applied through electrode E1 at the same time that a stimulus current of 0.1xI1 where applied through electrode E2, then the location within the tissue 54 where the stimulus would be felt would be a little to the right of the point 56, more or less somewhere on the line 62. If the stimulus current applied through electrode E1 continued to be deceased while, at the same time, the current applied through electrode E2 were increased, then the location in the tissue where the stimulus would be directed would move along the line 62 from left to right, i.e., from point 56 to point 58.

Similarly, by concurrently delivering current stimuli at electrodes E2 and E3, the location in the tissue where the effective stimulus would be felt would lie somewhere along the line 64, depending on the weighting of stimulus currents delivered at the two electrodes. This concept of current steering is described more fully in U.S. Pat. No. 6,393,325, incorporated herein by reference.

It is noted that the concept of virtual electrodes which directs a stimulus to a location on the cochlear location or place is broad concept. One method of implementing virtual electrodes is by concurrently delivering stimuli at two or more electrodes. Another way of implementing virtual electrodes is to present alternating stimuli at two electrodes in a time-multiplexed manner. For example, a first stimulus current is presented at the first electrode, then a second stimulus current is presented at the second electrode then, the first stimulus current is presented at the first electrode, then second stimulus current is presented at the second electrode, and so on, in a time multiplexed sequence. The first and second stimulus signals are usually different, e.g., they have different amplitudes and pulsewidths. Such delivery of stimulation will be perceived as if a virtual electrode were delivering a stimulus, which virtual electrode appears to be located between the two physical electrodes.

When an electrode array is implanted into one of the ducts of a cochlea, the spatial frequency represented by each electrode contact of the electrode array must correspond to the spatial frequency or "place" along the cochlea.

Figure 4A:
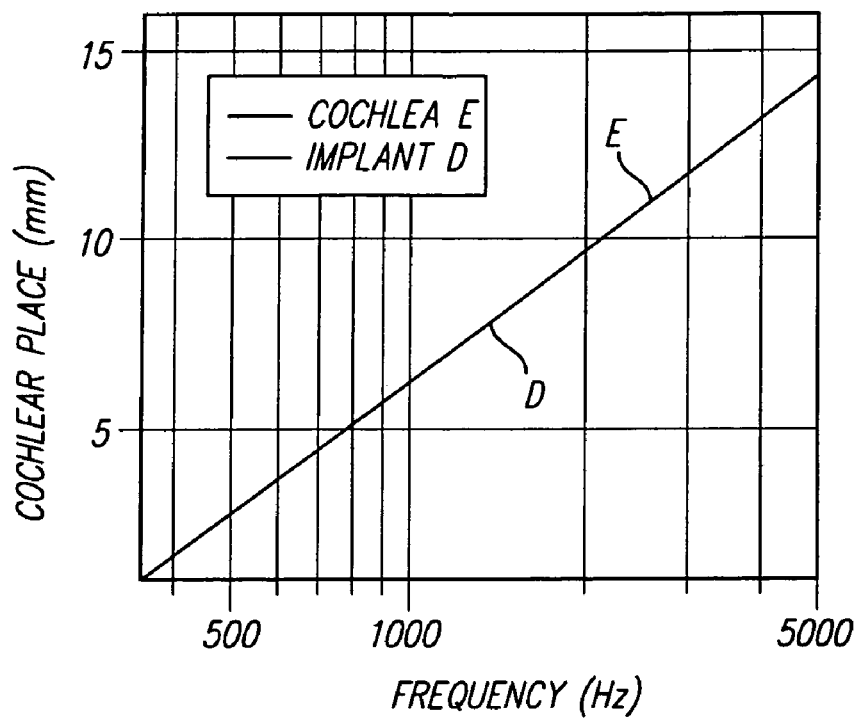
FIG. 4A shows a graph showing the intrinsic line E of an individual's cochlea that is defined by the relationship between cochlear location ("place") versus the log(frequency of perceived sound)

FIG. 4A shows the relationship between the cochlear place (mm) versus the associated audio frequency (Hz) of that place. The line E is referred to herein as the "intrinsic line" having an "intrinsic slope" for an individual cochlea. In the ear, each place along the cochlea corresponds to a specific perceived sound frequency. This relationship between cochlear place and perceived sound frequency is different for every individual, since no two cochleas are alike and the nerve wiring between the cochlea and to the brain is different for every individual. In addition, the implant fitting curve (line) which maps the cochlear place or electrode place versus perceived audio frequency will also be different for every individual. To properly perceive sounds, as produced through a particular cochlear system, including a specific electrode array, the implant system must be "fitted" or "tuned" to accommodate the individual anatomical differences, the particular configuration of the electrode array, as well as its particular placement in the cochlea.

Figure 4B:
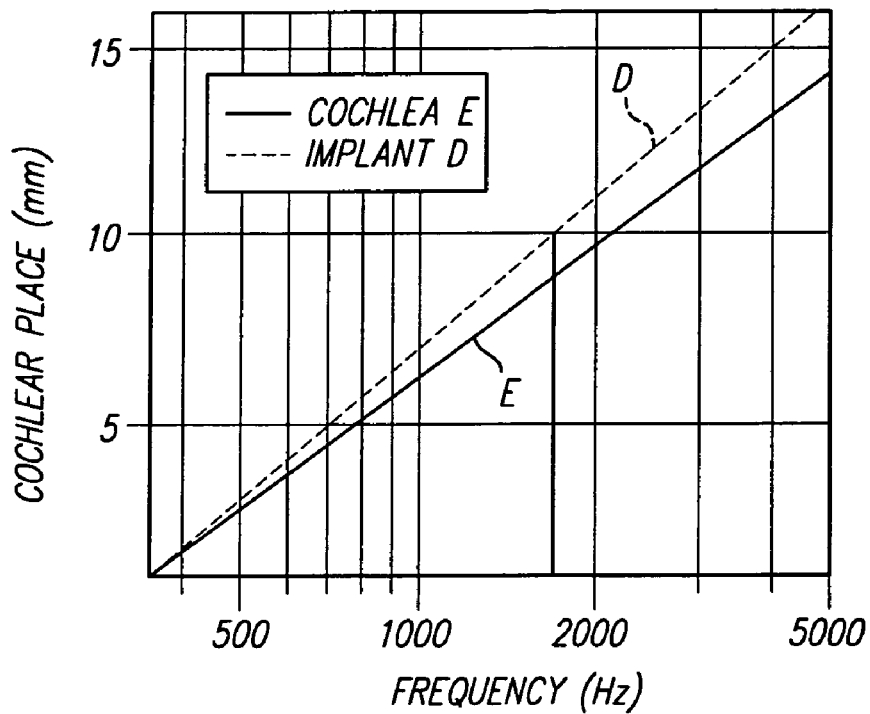
FIG. 4B shows another graph showing an intrinsic line E and a implant fitting line D showing both lateral and absolute misalignment that can be referred to as "pitch warping"

FIG. 4B shows two curves (lines), the lower line, E, represents the actual relationship between the cochlear place (mm) versus the associated frequency of that place. The upper line, D, represents the implant fitting line of the cochlear implant which is misaligned with the intrinsic line (and slope) E. This misalignment is sometimes referred to as a "pitch warping".

Assume that a 2000 Hz incoming tone is picked up (or generated) by the cochlear system. The cochlear implant user then should perceive a 2000 Hz tone. After the electrode array is implanted, a guess is made for what the correct implant fitting line D (including slope) should be. However, because of variability in an individual's anatomical cochlea, invariably the guessed fitting line D will not initially correspond to the intrinsic line E, as shown in FIG. 4B. The goal is to adjust (tune) the implant fitting line D to overlap the intrinsic line E.

From FIG. 4B, it can be seen that stimulation must be applied at a slightly different cochlear place than was originally guessed to yield a perceived frequency of 2000 Hz. For instance, the electrode and cochlear place to be stimulated is at about 11 mm for the intrinsic line D, not the predicted 10 mm for the implant fitting line E. Such pitch warping makes enjoyment of music difficult. Note, however, that if the electrode array position in the cochlea is altered slightly, either placed further into the cochlea or slightly out from the cochlea, the relationship of each "place" along the electrode array would again change in relationship. Thus, to determine the slope of the electrode array "place" along the electrode array and the corresponding audio frequency, the electrode array must be fixed during the fitting procedure.

The challenge is to match the fitting line D to the intrinsic line E. It would be ideal that when a 2000 Hz tone is presented through the cochlear system, that a perceived tone of 1700 Hz can be reported by the individual. But, most individuals cannot discern with precision that a tone is actually 1700 Hz and not 2000 Hz, unless the individual is highly musically trained and has perfect pitch.

There is now described an elegant method for determining the implant fitting curve (line) and the slope of implant fitting line. But before discussing the method, some concepts are first explained.

Figure 5A:
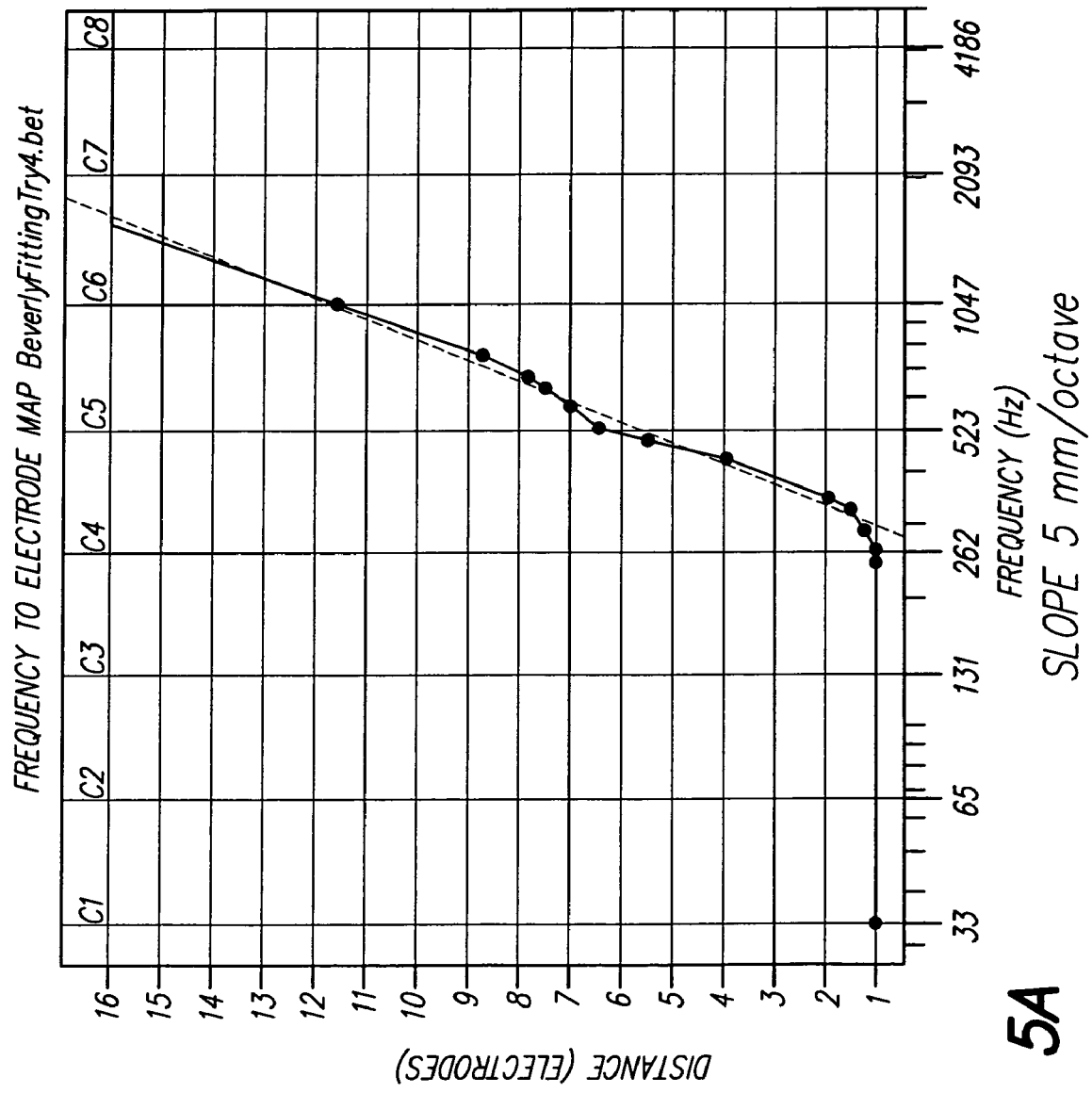
FIGS. 5A, 5B, and 5C show example implant fitting lines of three individual patients having cochlear implants, demonstrating that implant fitting lines on an cochlear distance versus Log(perceived frequency) plot are approximately linear over a large part of the perceived audio frequency range.
Figure 5B:
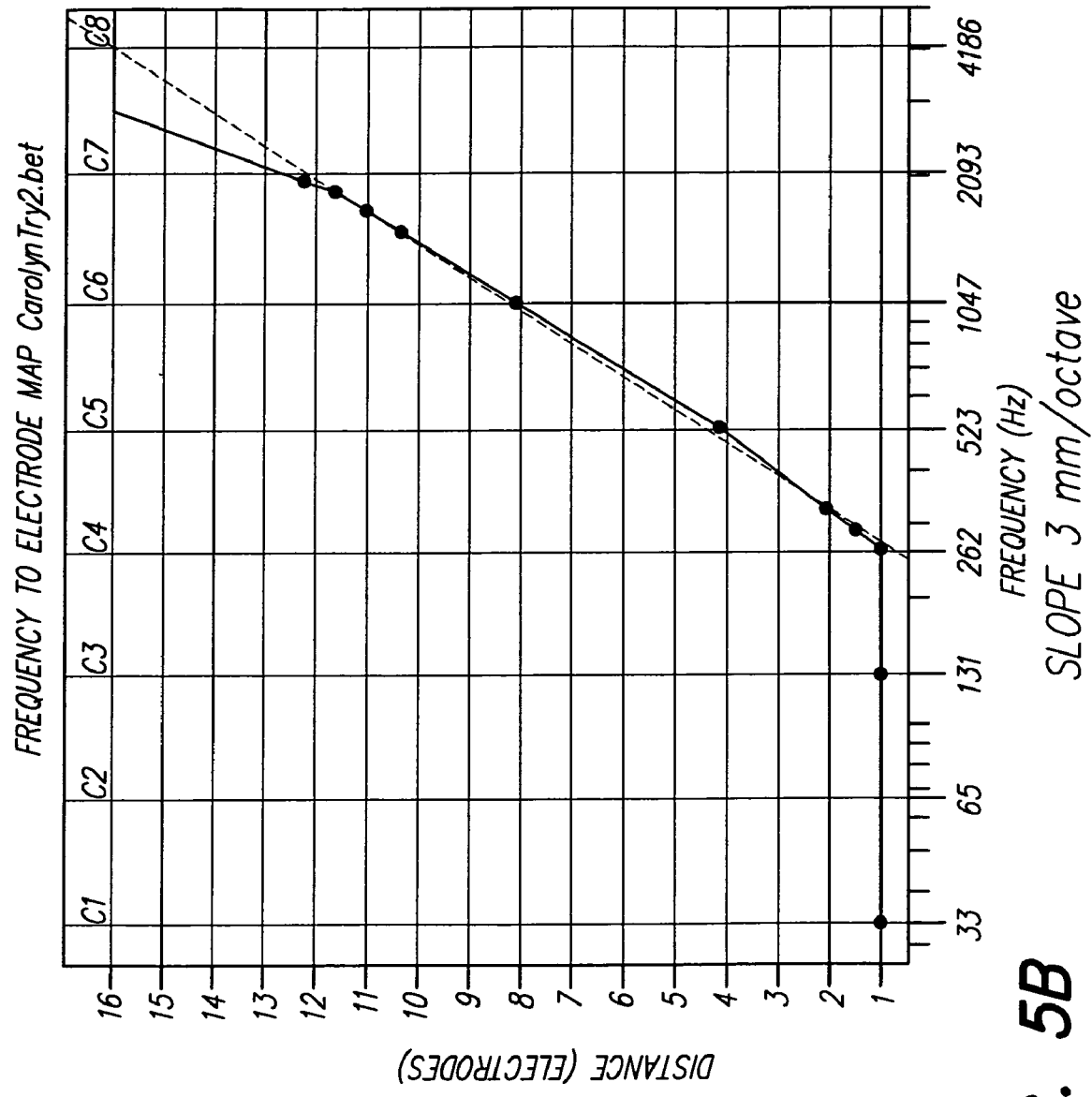
Figure 5C:
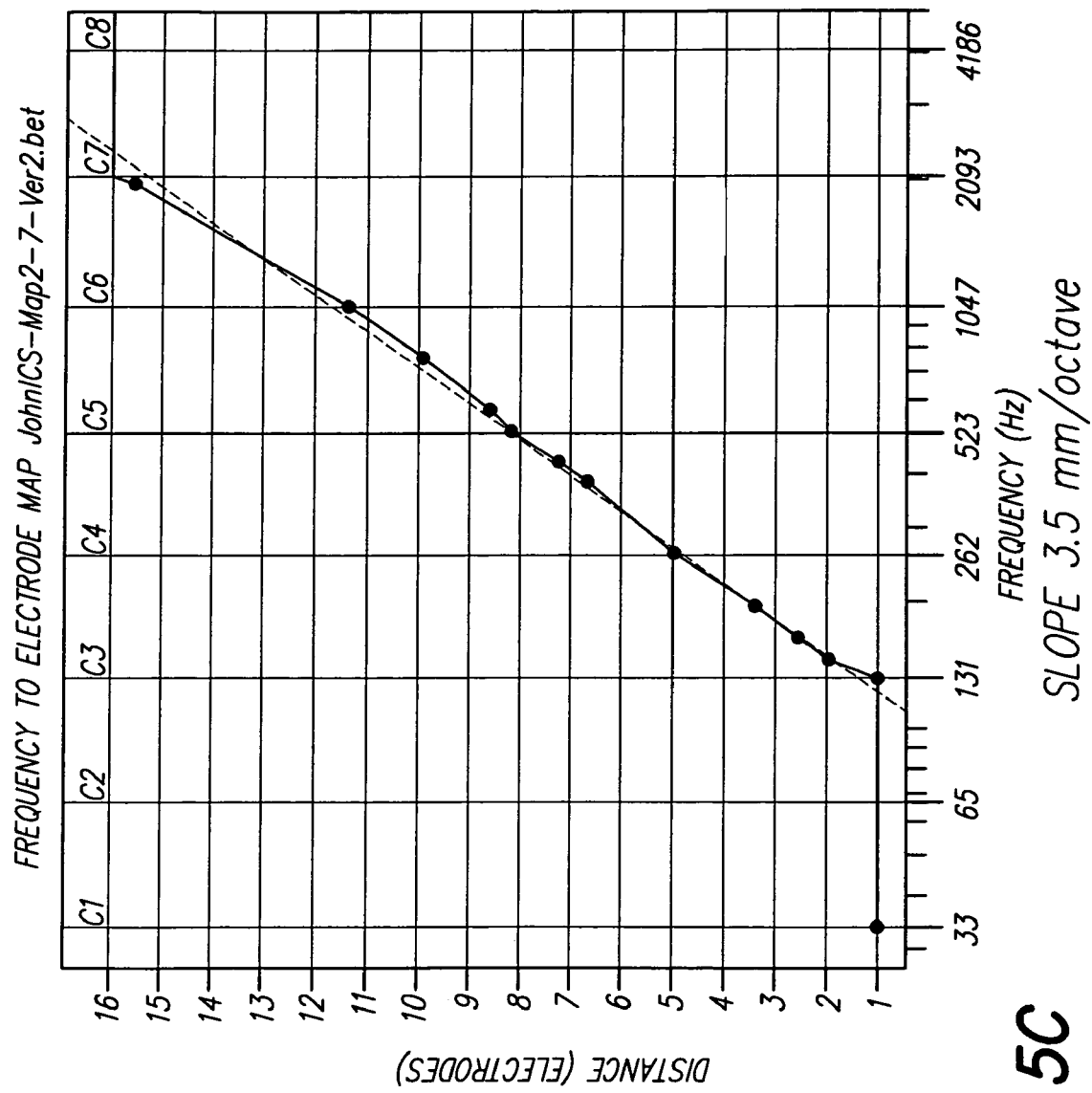

FIGS. 5A-5C illustrate the concept that in order to properly formulate a fitting procedure, the nature of the relationship between the cochlear "place" and perceived audio frequency must be understood. It has been discovered empirically, as shown in FIGS. 5A-5C that the relationship between the cochlear place (mm) versus the Log(perceived audio frequency (Hz)) is approximately linear for a large part of the perceived hearing range. It can be seen in FIGS. 5A-5C that with the electrode array implanted into the cochlea, a slope, calculated as the change in electrode distance or, alternatively, the cochlear place, over the change in log (frequency) may be obtained. It is an important fact that a good percentage of the audio frequency band is remarkably linear on a X-Log (frequency) plot, as this fact is utilized in the fitting procedure of the present method.

Another important concept to understand is that if the proper fitting slope is determined, the relationship of musical tones in a simple tune will be recognizable. With the correct slope determined and applied, even if the fitting line does not overlap the intrinsic line, a simple musical tune can be recognized, as each note in relationship to other notes in a tune will be in a harmonic relationship.

Figure 6:
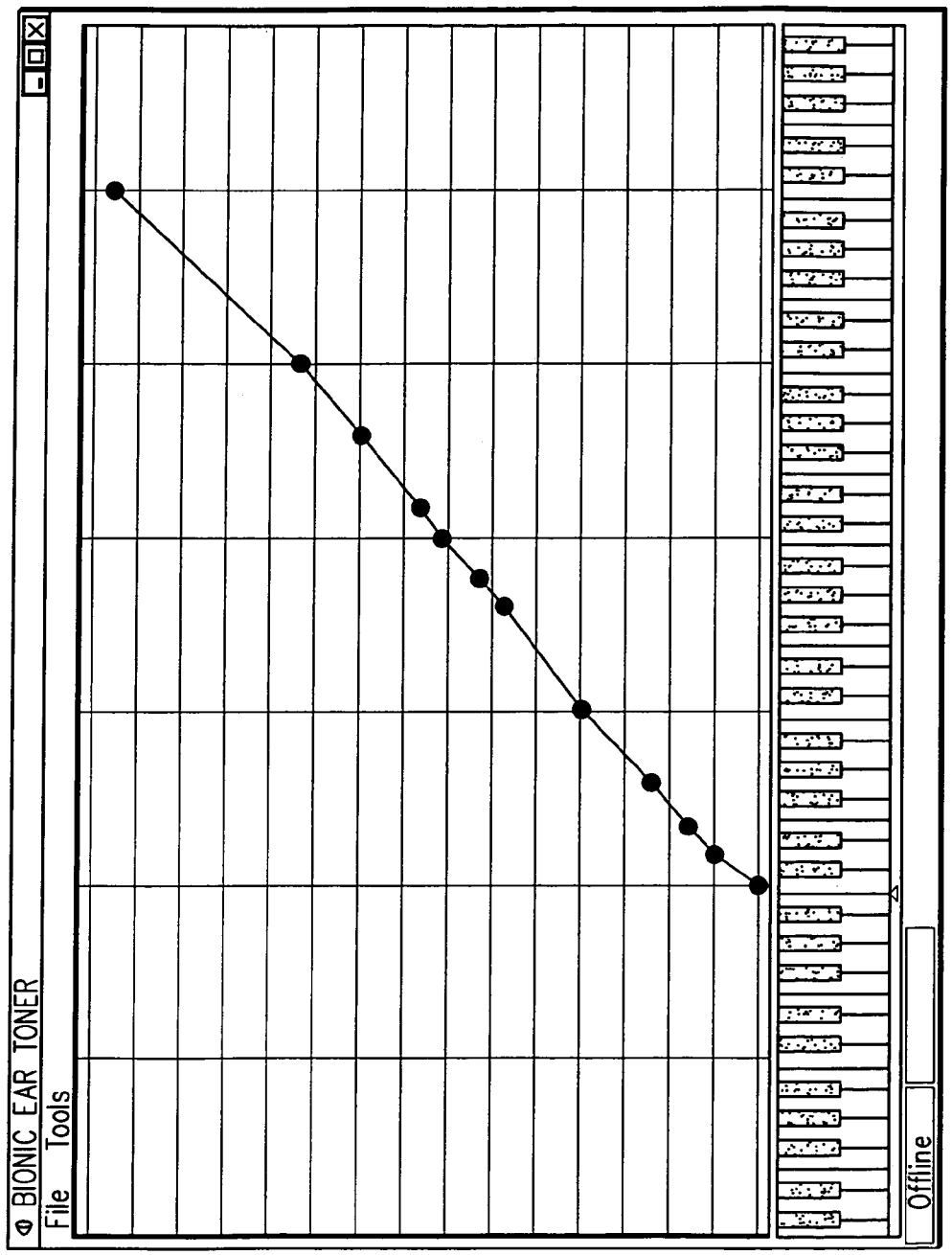
FIG. 6 shows a representation of the relationship between cochlear place and perceived frequencies (notes)

FIG. 6 represents, in a simplified way, the relationship of musical notes to cochlear place. The place on the cochlea corresponds to notes on a musical scale, as represented by notes on a piano scale. Thus, for the appreciation of music, it is important to determine the correct implant fitting slope or "relative alignment" which is parallel to the intrinsic line and intrinsic slope.

Figure 7:
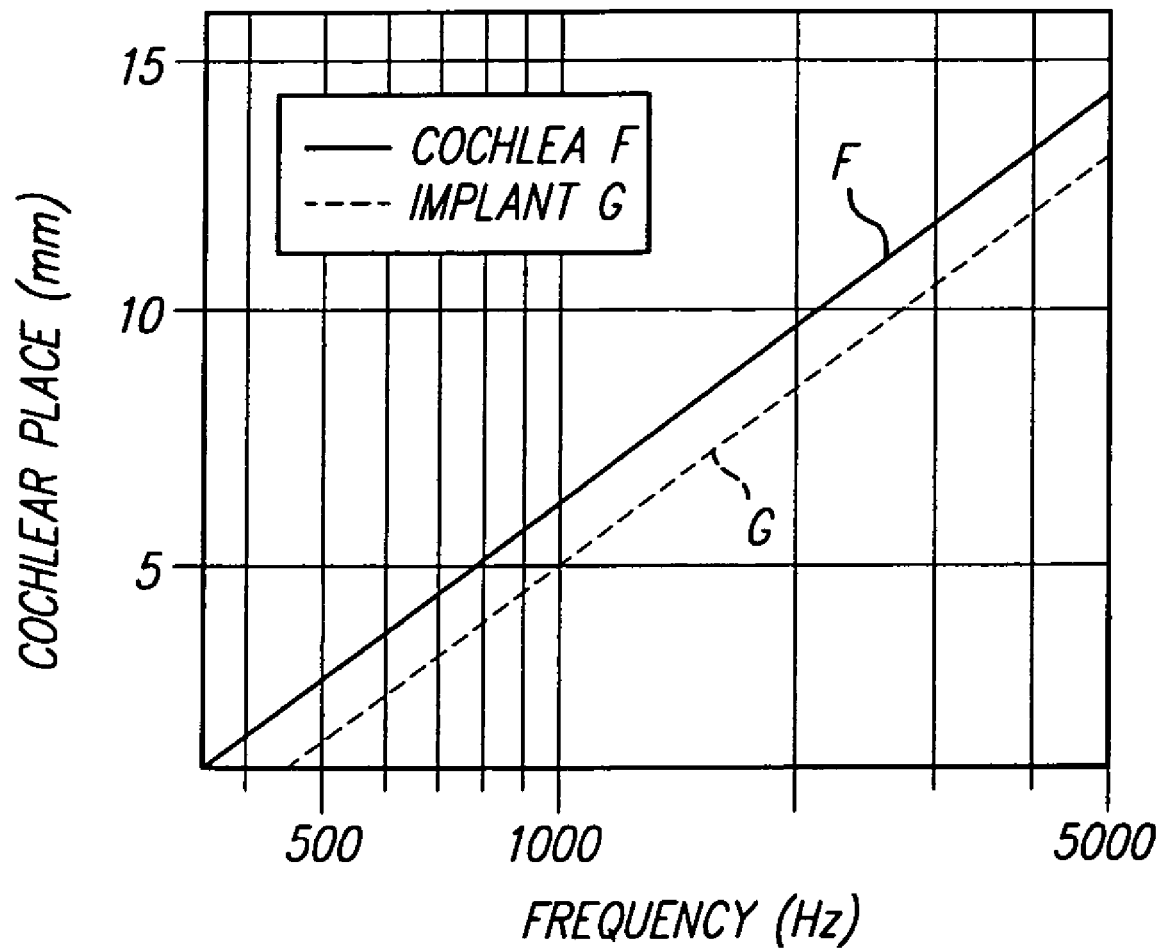
FIG. 7 shows an intrinsic curve (line) and an implant fitting curve (line) that are laterally aligned, i.e., the slopes are matched, but in which the two lines are not absolutely aligned, i.e., they are offset.

FIG. 7 shows a situation where the implant fitting line G and intrinsic line F have the same slopes. Thus, the implant fitting line and the intrinsic line are in relative alignment. Line F represents the intrinsic cochlear slope of the log(perceived sound frequency) versus the cochlear place. Line G represents the implant fitting slope of the relationship between electrode position, e.g., the first electrode at the proximal end of the electrode array, versus the log(perceived sound frequency). As discussed, to appreciate music, it is only necessary to align the implant fitting slope, line F, to have the same slope as the intrinsic line G. This is because the relationship of musical notes (tones) continue to remain in harmonic relationship between notes, even though there may be an offset between lines F and G, as shown in FIG. 7.

The offset, however, does determine the overall pitch of sound that is perceived. That is, the overall pitch of the sound may be either too low or too high, if the implant fitting slope of line F is not perfectly aligned with the intrinsic slope of line G. When there is a misalignment, such that line F is offset to the right of line G, the perceived sound may sound "pinched", "squeaky" or "tinny". If the Line F is offset to the left of line G, the perceived sound may be described as too low.

The effect of offset, i.e., error in absolute alignment, is particularly important in sounds having a characteristic pitch. This is especially true of human speech which has a recognizable overall pitch. The presence of an offset, for example, line F to the right of line G, can cause male speech to be too high or "squeaky." This is not unlike the effect of playback on a record player or tape recorder at too high speed. Conversely, line F offset to the left of line G can cause male (or for that matter, female speech) to be too low and be perceived as a slow, low frequency drone. This is not unlike the effect of playback on a tape recorder at too low a speed.

With understanding of the relationship between the cochlear place and the resulting perceived audio frequency, an implant fitting routine may be formulated. The fitting routine must satisfy the following basic requirements: (1) the method must be capable of being performed quickly in a clinical setting and (2) the method must yield an accurate result.

The method described herein satisfies the above two requirements. An embodiment of the present method may be summarized as comprising at least two major steps: (a) determining the individual's fitting slope, using a particular electrode array by presenting tunes embodying different fitting line slopes and (b) determining the offset or lateral alignment of the implant fitting line by presenting a known sound having characteristic pitch, e.g., speech.

An individual's implant fitting slope depends on the individual's anatomy, the electrode array configuration used, and the position of the electrode array relative to the cochlea. Determining an individual's implant fitting line (including the slope), quickly and accurately, is not a trivial task. At first glance, it would appear that providing various tones through the electrode array could be used to determine the fitting line, so that it matches the intrinsic line, as in U.S. Provisional Application 60/433,037, filed Dec. 11, 2002, which application is herein incorporated by reference. Using audio tones to obtain the fitting slope, however, is best suited to the highly musically trained individual, as such individuals are generally able to distinguish between different tones and convey such differences to a clinician.

The present disclosure uses musical tunes to determine the fitting slope both quickly and accurately in any individual, including non-musically trained individuals. The use of musical tunes to determine the slope is not immediately obvious. A simple, familiar musical tune, however, is a good reference to use because the relationship of notes within such a tune can be quickly assessed for whether the notes are "harmonic." An individual, without musical training, can easily and quickly identify whether a tune is too compressed, i.e., the frequency range is too compressed, and therefore the notes sound too much alike or the frequency range is too expansive, such that the notes are perceived to be to far apart than remembered. In addition, when the tune is played with different fitting slopes, a patient can quickly assess whether one rendition of a musical tune, presented with a particular implant fitting slope, sounds better than another rendition presented with a different implant fitting slope. When the implant fitting slope is correctly determined, a musical tune will sound most like a remembered musical tune.

The present method is notable because determination of the implant fitting slope of the implant fitting line does not require special musical training. A subject can quickly ascertain the relationship of one note to the next simply by remembering what a particular tune, e.g., "Twinkle-Twinkle Little Star" should sound like. Not only is the method accurate, but the method can be completed relatively quickly in a clinical setting because such musical melodies, presented with different fitting slopes, can be quickly implemented with appropriate programmable software. Because the method is based on the subject comparing a presented tune with her memory of the tune, the described methods are particularly suited for those subjects that have had previous auditory experience. If the patient was pre-lingual at the onset of deafness, then the patient has not had the experience necessary to recognize familiar musical melodies and is not a candidate for this fitting method, as described further below.

In some embodiments, the method described herein takes advantage of recent developments in stimulation technique—that is, the concept of virtual electrodes. Without use of virtual electrodes it would be difficult, if not impossible, to accurately stimulate the cochlear place to represent or "play" a tune. This is because in a typical 8 to 22 electrode contact array, the individual electrode contacts do not provide the required resolution necessary to stimulate the appropriate precise points on the cochlea. The employment of virtual electrodes, however, facilitates the precise stimulation required by the present fitting method to use musical tunes as a probe.

Figure 8A:
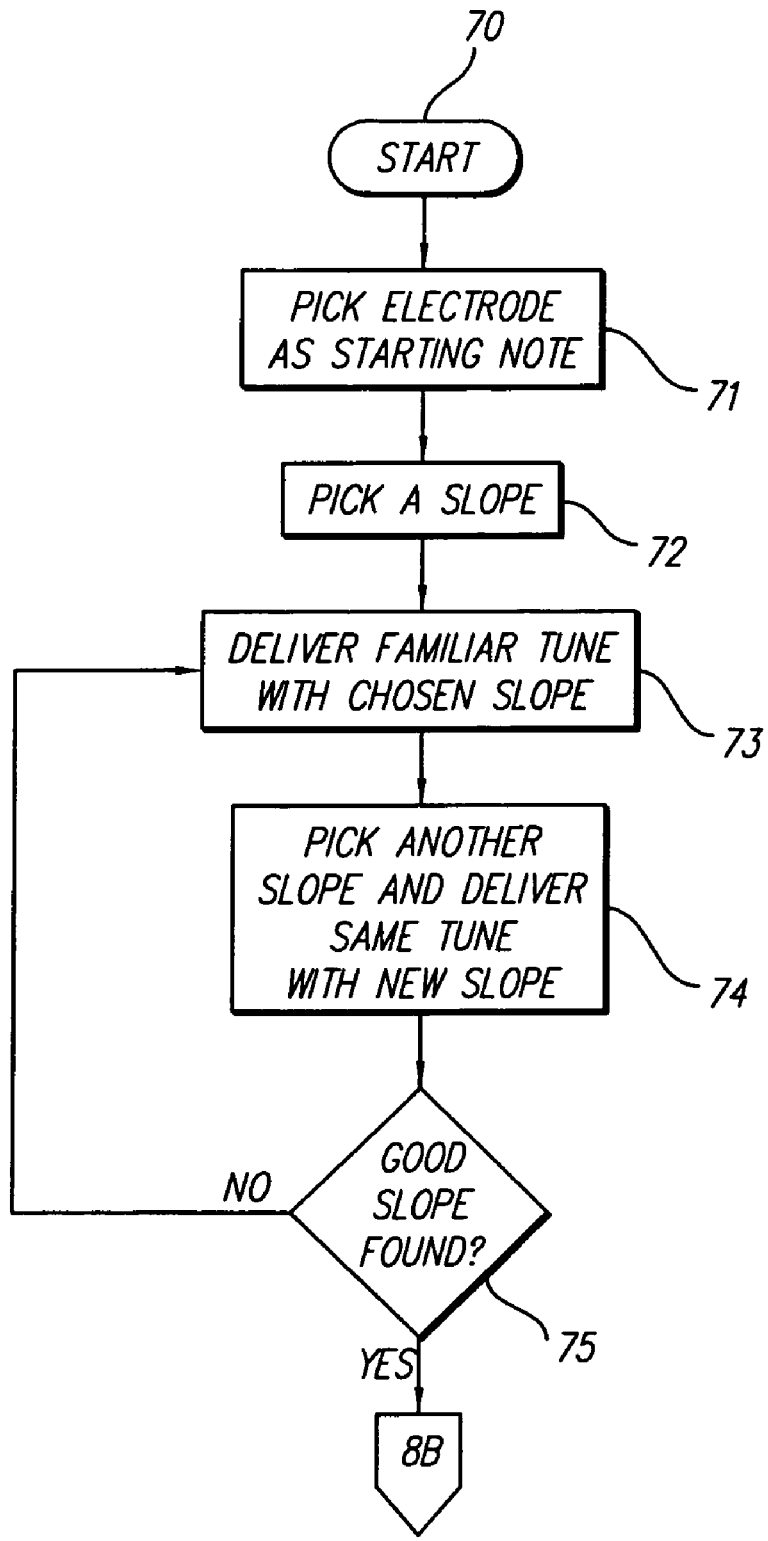
FIGS. 8A and 8B present a flowchart that outlines one embodiment of a method for determining the optimal implant fitting curve (line)
Figure 8B:
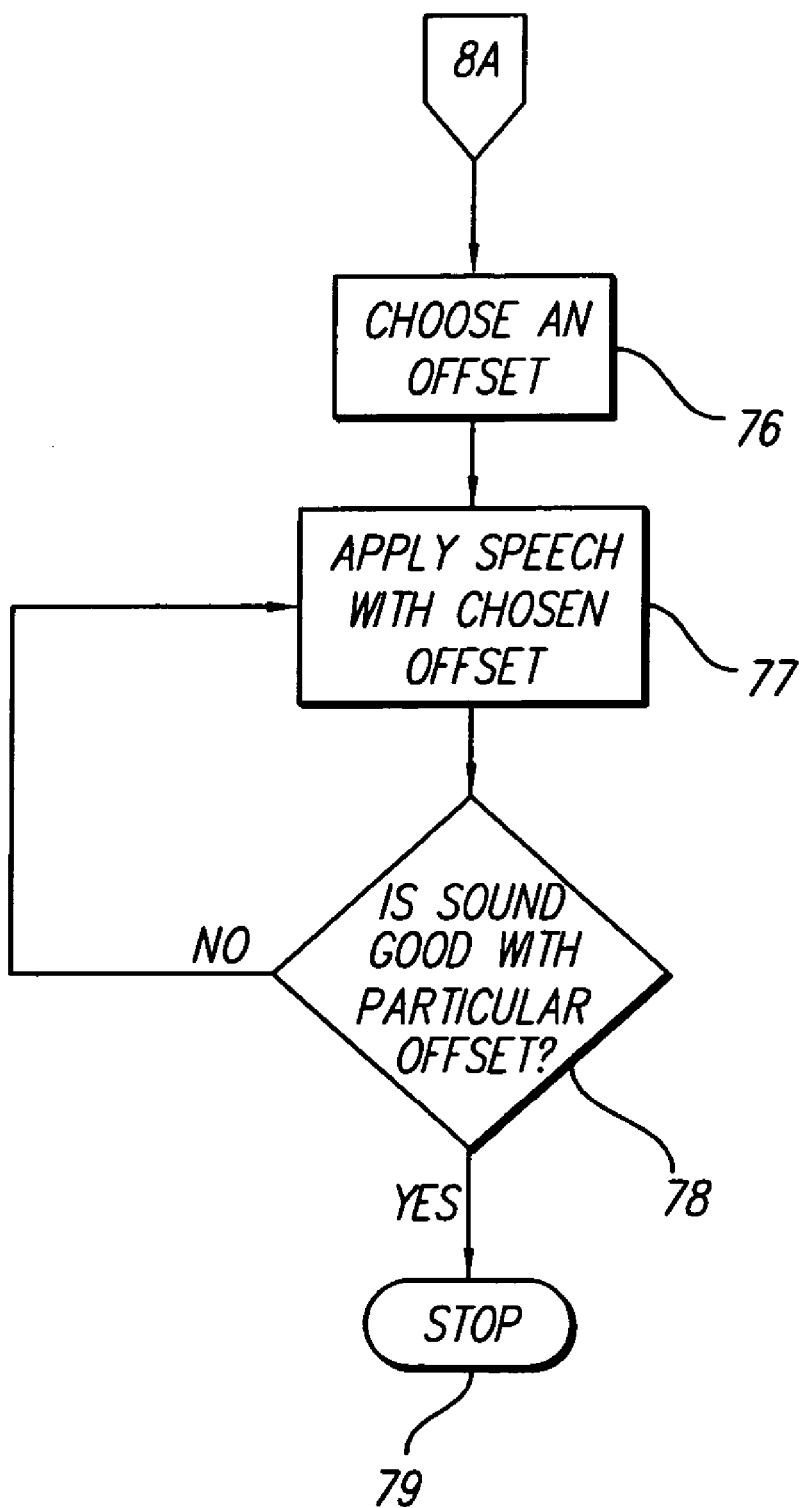

The method is described in connection with the flow chart shown in FIG. 8A and continuing in FIG. 8B. Each step in the method shown in FIGS. 8A and 8B is summarized in a "block". The relationship between the steps, i.e., the order in which the steps are carried out, is represented by the manner in which the blocks are connected in the flow chart. Each block has a reference number assigned to it.

The method can be simplified into two major parts: (a) determining the slope of the implant fitting line that relates Log(frequency of sound) to the "place" or location along the cochlea ("relative alignment") and (b) determining the offset of the implant fitting line ("absolute alignment"). It may be possible to simply perform part (a) without further proceeding to part (b) and this is included as one embodiment. The best fitting routine, however, is performed by including both parts (a) and (b).

Referring to FIGS. 8A and 8B, a simplified flowchart is provided which further illustrates the method of quickly optimizing the fitting of a cochlear implant. The starting point is step 70 within the ellipse. The next step is shown in box 71, where one electrode (or the frequency assigned to that electrode) is picked as a starting location corresponding to the first note of a familiar song or tune. This electrode can be used each time as the spatial or place location of the first note of a song or tune presented. It is emphasized that this is for the sake of convenience, and that if desired, a place half way or somewhere between the location of the two electrodes, e.g., a virtual electrode location, can be chosen as the anchor location for the first note. The next step, indicated by box 72, is to pick a predetermined slope, i.e., the slope of the graph Log (frequency) versus cochlear place. While this slope can vary from individual to individual, a predetermined (guessed) slope can be chosen based on known averages of intrinsic slopes of individuals. This, at least, provides a rough ballpark slope of the implant fitting line as a starting point. Next, as shown in box 73, a familiar tune or song is chosen, such as, for example, from a menu of tunes (songs) and the tune is presented to the patient. In presenting the tune, each following note, based on the chosen slope, will be precisely presented on a cochlear location or "place" by implementing the concept of virtual electrodes.

As discussed, virtual electrodes may be created in at least two different ways. First, virtual electrodes may be created by delivering weighted currents to two electrodes such that the effect is perceived as an electrode somewhere in between the electrodes. Another possible way to create virtual electrodes is to rapidly alternate stimulation in a time-multiplexed manner between two electrodes. In other words, a stimulus is applied at electrode E1 and then, a very short duration of time later, a stimulus is applied at E2 and then, a very short duration of time later, a stimulus is applied at E1, and so on. The effect of such rapid, time-multiplexed delivery of stimulation is to create a virtual electrode having a "place" located somewhere between the space of E1 and E2. As explained previously, notes following the first anchor note of a tune will be presented ideally with virtual electrodes which increases the resolution of stimulus presentation on the cochlea.

Next, as shown in box 74, the implant fitting slope can be changed and the same tune or song can be presented to the patient starting at the same anchor electrode, with the same first note. The patient then compares the original rendition of the tune with the second rendition to see which one sounds more like the tune, as remembered by the patient. The patient can record which slope is better. At this point, the patient may choose to stop if the rendition is sufficiently close to the remembered tune but, usually, more slopes are presented and more renditions of the same tune are presented as represented by the return arrow back to box 74 from decision box 75. Based on the last response, another slope can be interactively chosen and the same tune once again can be played. In this iterative process, the values of implant fitting slopes presented should begin to converge to a best value of the fitting slope, where incremental changes to the slope do not improve the quality of the tune as perceived by the cochlear implant wearer.

Perhaps the best analogy of the iterative fitting process for determining the implant fitting slope is to analogize to the procedure for fitting eye glasses. The process for determining lens strength (diopters) is accomplished by presenting various lenses with various lens strength in a manner to "zero in" on the optimal lens prescription. The method requires starting with a lens of a particular prescription. Another lens strength is picked and then the better of the two is picked. Armed with this knowledge, a third lens may be selected and presented, and so forth, until a final, best lens is determined. The same iterative converging process may be used to determine the correct implant fitting slope.

Once no appreciable difference is detected between two very close implant fitting slopes, one of those slope values can be chosen. The "relative alignment" portion of the process is now complete. As mentioned, it may be possible to simply perform the relative alignment process without further proceeding to the "absolute alignment" process. The best fitting routine, however, is performed by including the absolute alignment process, which is described beginning with the next step, shown in box 76 of FIG. 8B. In this step, a predetermined (guessed) offset of the implant fitting line is selected.

Figure 9A:
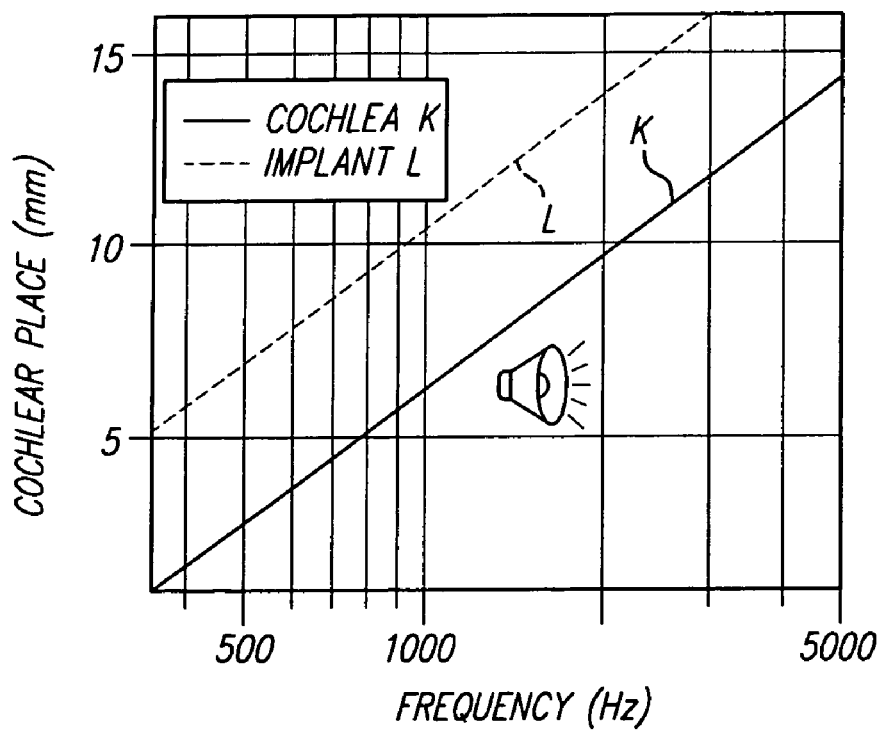
FIGS. 9A, 9B and 9C show intrinsic line K and implant fitting lines L and M, which latter two lines are corrected for slope but do not have the correct offset relative to the intrinsic line K.
Figure 9B:
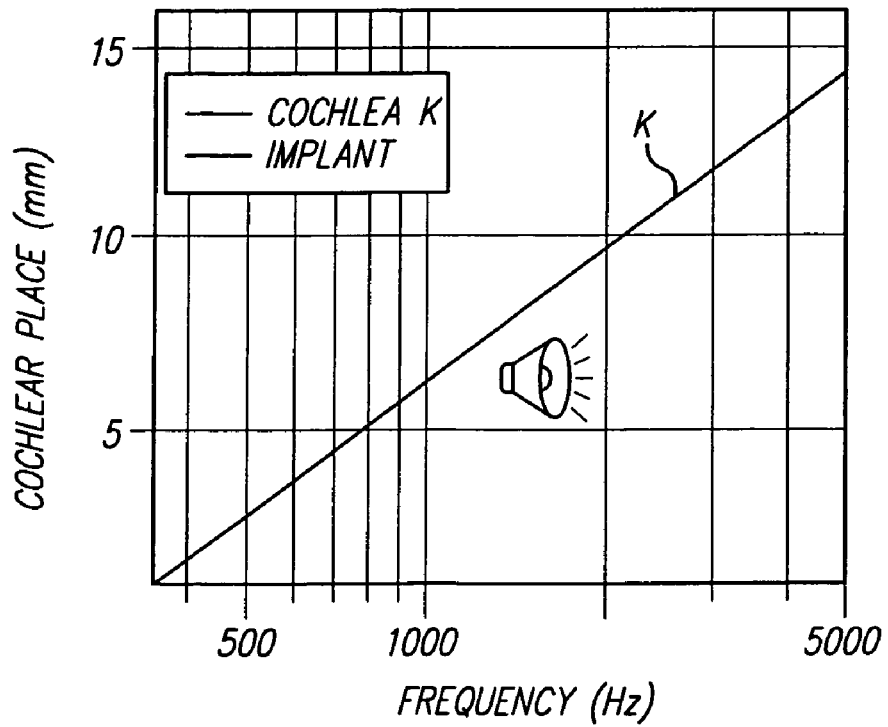
Figure 9C:
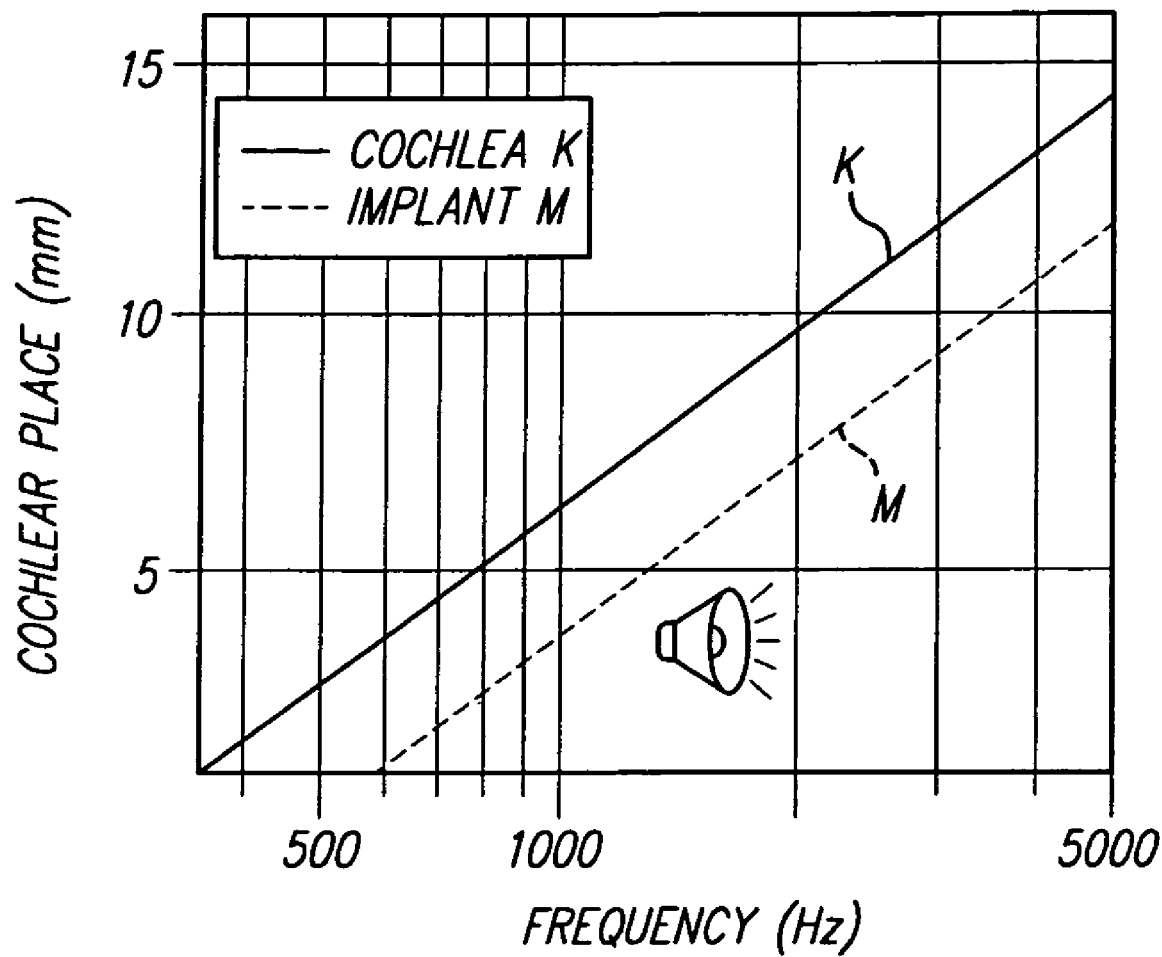

The offset is the error in absolute alignment, which is described in more detail with reference to FIGS. 9A-9C, which illustrate error in absolute alignment using graphed lines K, L and M. Note that the slopes are the same for each line and therefore there is no lateral misalignment. FIG. 9B shows the intrinsic slope of line K for an individual's cochlea, which slope relates the log(perceived audio frequency) to the cochlear place. FIG. 9A shows a line L offset to the left of line K. Line L is the fitting curve (line) of an implanted cochlear implant, with an offset error. It is expected that the overall sound perceived will have a lower pitched than remembered. FIG. 9C shows line M offset to the right of fitting curve (line) K. The overall sound perceived with fitting curve K will be higher pitched than it should be or remembered.

To eliminate this error in absolute alignment, another sound probe other than musical tunes is used. Musical tunes are not the best probes for correcting the offset because tunes do not have an intrinsic "correct" pitch. Tunes may be played in different keys, with different overall pitch, and yet may be recognizable as musical tunes because each note in the tune remains in harmonic relationship to other notes in the tune.

Other sounds, however, are associated with a known pitch. For example, a chirping bird, a cricket sound or rain drops falling or sea surf sounds have a characteristic pitch that can be remembered. The best sound to use as pitch reference, however, is human speech, not only because it is important, per se, to optimize the implant system to sufficiently convey speech, but also because the human hearing system, including the associated nervous system, is especially sensitive to the pitch of human speech.

Referring again to FIG. 8B, indicated in box 76, a predetermined offset is chosen. This predetermined offset can be a guess based on empirical data of averaged values of intrinsic lines of individuals, using the particular electrode array and cochlear system. This guessed offset will be applied to the first presentation of speech as shown in box 77. Next as shown in box 78, the patient can compare the perception of speech to remembered speech. Obviously, if it is male speech, but the speech sounds more like female speech, the offset is incorrect. In that case, the offset of the implant fitting line must be adjusted leftward to lower the overall pitch.

If the offset is not the best one, the decision step 78 indicates a return line back to box 76, in which the offset is adjusted and the same speech, with the new offset value, is then presented for comparison, as represented in box 77. As shown by the step 78, a comparison of the overall pitch of the previous speech with the current speech is again made and a decision can be made to record the speech rendition with the particular offset having the better or more natural sounding overall pitch. Based on this decision, another offset may be chosen returning to the step in box 76 and the same speech may be presented in box 77. The offset value should converge to a value wherein further increments to the offset become smaller and do not provide appreciable improvement in the overall sound pitch. After step 78, when the best offset is determined, this last, best offset value can be used to determine the implant fitting line. Thus, at the end of the method signified by stop 79, the method will yield both a slope and an offset defining the best implant fitting line.

The basic steps described above are best implemented with user controlled software to make the process efficient and accurate in a clinical setting.

Figure 10:
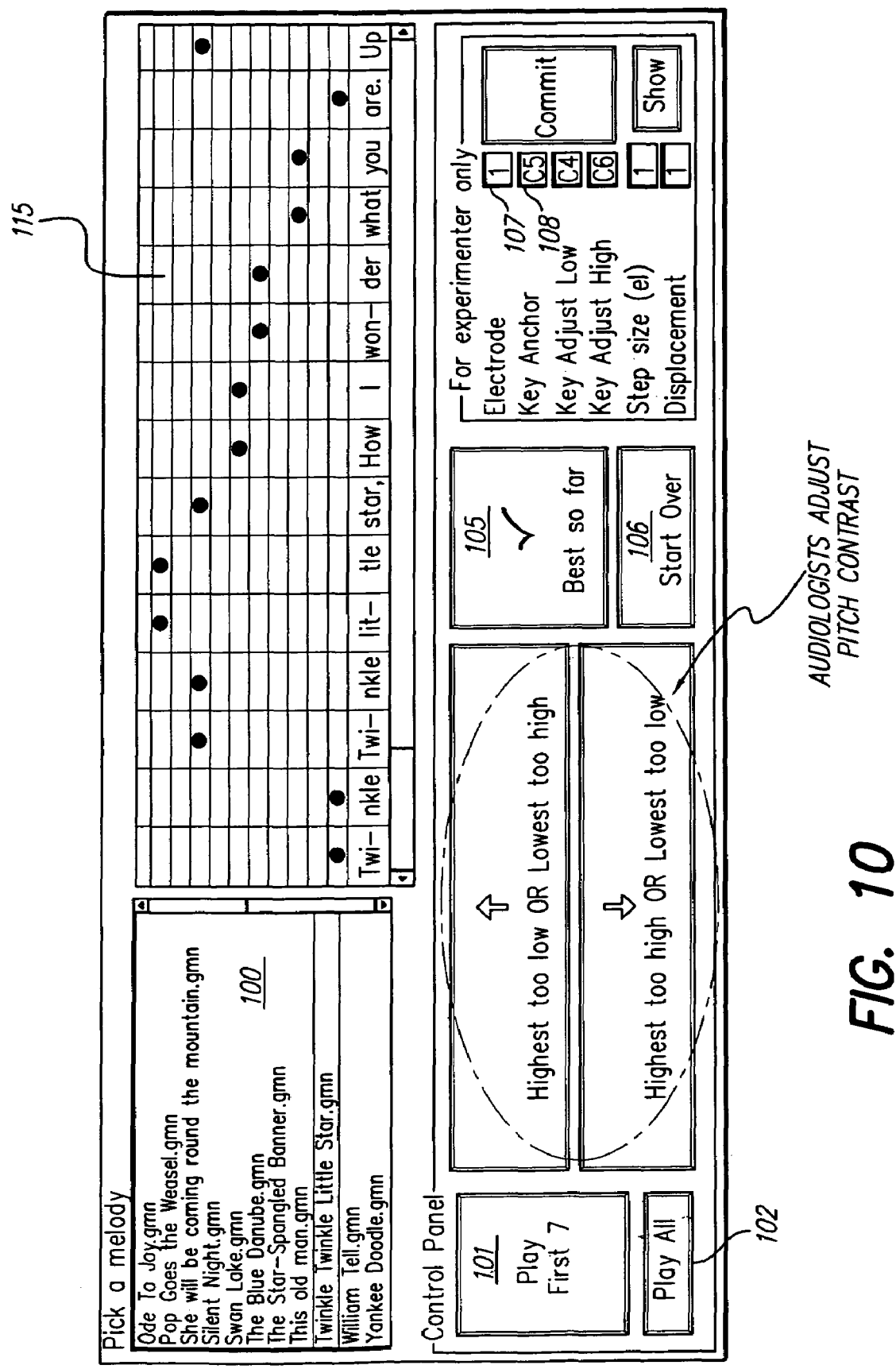
FIG. 10 shows an example software interface menu that may be used to implement the disclosed methods.

FIG. 10 shows an example of a menu interface to a computer software program that can be used to implement the steps presented in FIGS. 8A and 8B. The menu interface can have, for example, a selection of tunes 100, so that a patient can select a short, familiar tune used for the remainder of the fitting/tuning process. By selecting key 101, using a cursor for example, the patient or software operator can play a predetermined number of notes, such as, for example, seven notes, of the chosen tune. On the other hand, by selecting key 102 a complete melody can be played. Selecting key 103 increases the implant fitting slope, whereas selecting key 104 decreases the fitting slope. Key 105 is selected to indicate that a current step (slope) size is the "best so far" among the renditions presented, that have different step (slope) sizes. Key 106 is selected to restart the entire fitting process. Other parameters can be pre-programmed before the play. For example, Key 107 may indicate the first or starting electrode. Key 108 may indicate the anchor point on the slope, the electrode, or cochlear place, about which the fitting line is rotated to change the fitting slope. The frequency or note which is assigned to this anchor electrode or anchor cochlear place may be kept constant throughout the process of determining the fitting slope.

Figure 11:
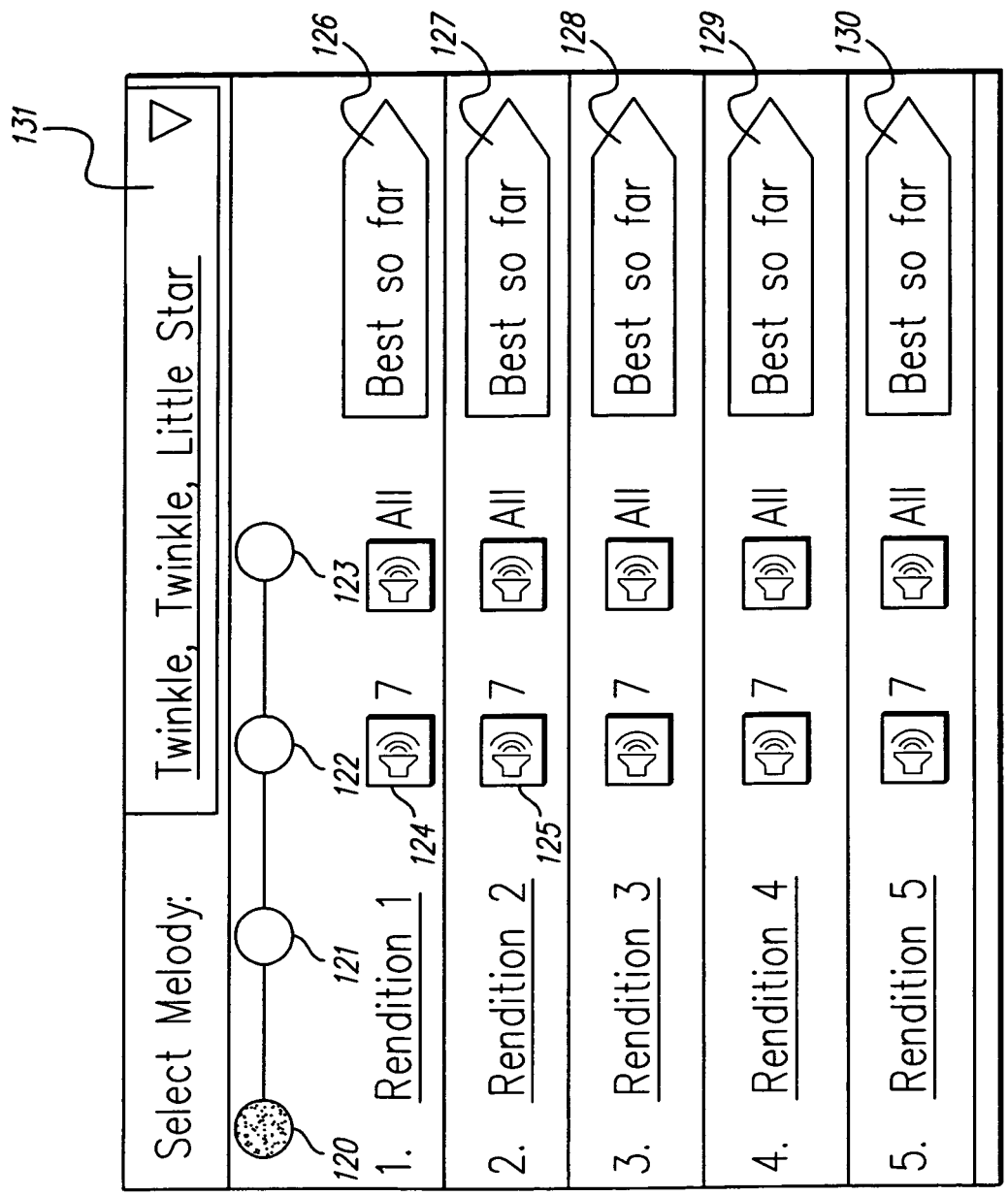
FIGS. 11 and 12 show example software interface menus that may be used to implement an iterative process to determine the slope of the implant fitting line.

FIG. 11 further illustrates an example implementation of the fitting process in which the best implant fitting slope is determined. Displays or lights 120-123 may indicate what current step (slope) size is being presented. Keys 124, 125 may be selected to play the first 7 notes of a familiar melody but at different fitting slopes. Keys 126-130 may be used by the patient or software operator to record which one of the presented musical renditions associated with a given step (slope) size provides the best musical result. Display 131 indicates the current tune or melody that is being played.

Figure 12:
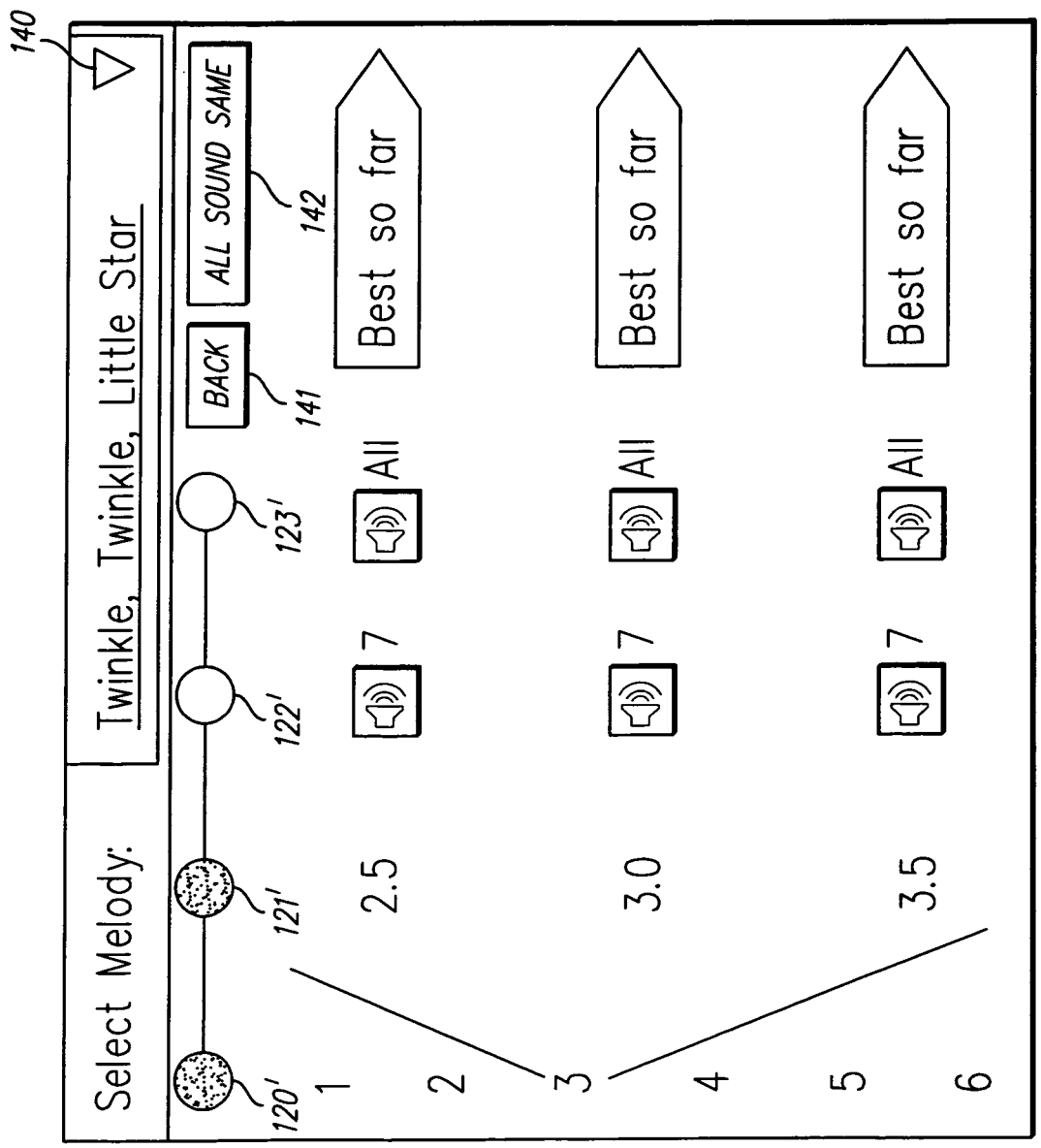

FIG. 12 illustrates a continuation of the fitting process to determine the best slope of the implant fitting line. Display 140 shows the tune/melody that has been selected. Displays 120', 121', 122', and 123' indicate the tune having a particular slope value is being played. Key 141 is selected, for example, to go back to a rendition having a larger offset. The possible offsets shown are 2.5, 3, and 3.5. These indicate that the slopes being presented at 2.5 and 3.5 are half-steps (slopes), after rendition 3 has been first chosen from FIG. 11. This process is use to converge to the best fitting slope. The half-steps shown, however, are arbitrary values and other values of steps sizes with different markings or labels may be used to indicate a musical rendition with a particular offset value. After all three renditions 2.5, 3 and 3.5 are played, one of them may be marked or recorded as the best by selecting one of the "Best so far" keys. This iterative process may continue further until the best slope is found.

The next step of the fitting process is to determine the fitting offset to provide absolute alignment of the implant fitting line to overlap the intrinsic line. The same iterative process can be used as shown in FIGS. 11 and 12 to converge to the best offset value, using the same speech (or another sound having a characteristic pitch) each time, but presented with different offsets.

It is emphasized that FIGS. 10, 11, 12 represent only an example of interface menus that may be employed to implement the fitting method. Other types of menus may be used and such other implementations for carrying out the present fitting method are within the scope of the present claims.

Figure 13:
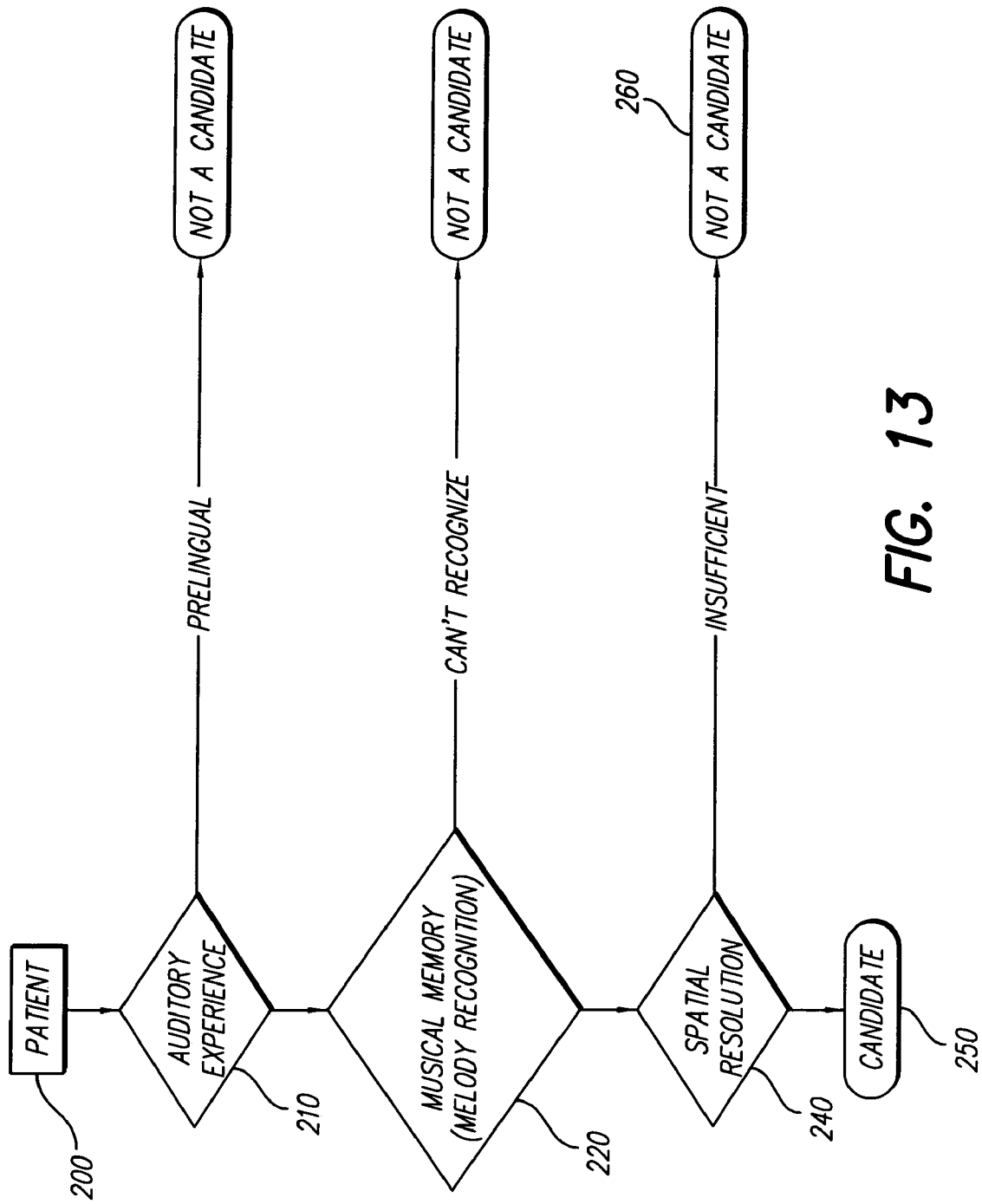
FIG. 13 shows a flowchart for ascertaining which patients are candidates who might benefit from the fitting tool.

FIG. 13 provides a flowchart for determining which patient 200 is eligible to undergo a cochlear fitting using simple musical melodies. The first selection criteria is provided in box 210—does the patient have auditory experience? If the patient was pre-lingual at the onset of deafness, then the patient has not had the experience necessary to recognize familiar musical melodies and is not a candidate for this fitting method. The next selection criteria is provided in box 220, where it is determined whether the patient has musical memory. In other words, is the patient capable of recognizing musical melodies? If not, the patient is not a candidate. The third criteria, represented by box 240, is whether the patient has sufficient spatial resolution. That is, if the patient cannot distinguish fine differences in the cochlea, i.e., the place in the cochlea, because of a defect such as an insufficient density of viable ganglion nerve cells in the cochlea, then the patient is not a candidate. If all criteria is met, then the patient is a candidate, as represented by box 250.

In summary, there is described herein a solution to quickly and accurately fit a cochlear implant in order to reduce pitch warping, so that patients can enjoy music and enhanced speech. The method can be simplified into two major parts: (a) finding the slope of the relation between Log(frequency of sound) and the "place" or location along the cochlea and (b) finding the offset of the implant fitting line. It may also be possible to simply perform part (a) without further proceeding to part (b), and that would be included as an embodiment of the method, however, a particularly advantageous fitting can be performed by including both parts (a) and (b).

There is now described alternative method of optimizing the pitch allocation in a cochlear implant using simple melodies. Pursuant to this method, a simple melody is presented to a user fitted with a cochlear implant. The melody comprises a series of tone bursts, each tone burst having a predetermined frequency and duration. The melody can be a predetermined melody that the user is likely to be familiar with through memory. For example, the melody can be "Mary Has a Little Lamb", which is a melody to which a large number of people have been exposed. After the user listens to the melody, the user determines whether the melody conforms to the user's memory of that melody. If the answer is yes, then the pitch allocation in the user's cochlear implant is likely optimized or close to being optimized. However, if the melody does not sound correct to the user, then the pitch allocation in the user's cochlear implant is likely incorrect. The user is then iteratively presented with distorted versions of the melody with the frequencies of the tones in the melody being distorted in a predetermined manner until the melody sounds "correct" to the user. It should be appreciated that the melody in the distorted state will not sound correct to an independent listener because the melody has been distorted. The program of the cochlear implant is then adjusted such that the distorted melody sounds "incorrect" and the original, actual melody sounds correct. The amount of adjustment to the program is determined based on the amount of distortion that was presented in the melody. In this manner, the programming of the cochlear implant is corrected so that the original melody sounds correct to both the cochlear implant user and to the independent listener who is not fitted with a cochlear implant.

Figure 14:
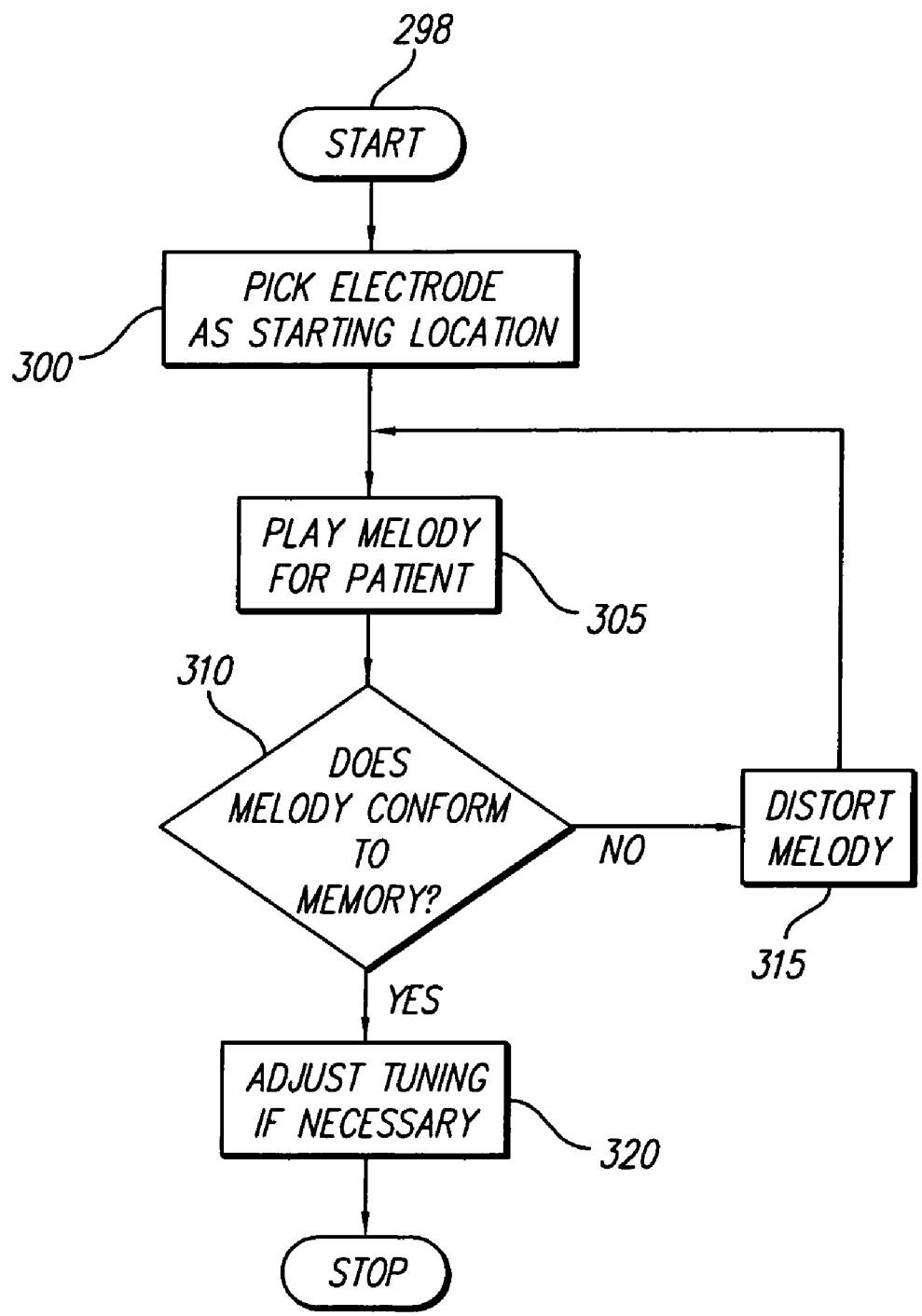
FIG. 14 shows a flowchart that outlines one embodiment of a method of pitch allocation in a cochlear implant by presenting distorted versions of melodies to a patient.

This process is now described in more detail with reference to the flow diagram shown in FIG. 14. Each step in the method shown in FIG. 14 is summarized in a block. The relationship between the steps i.e., the order in which the steps are carried out, is represented by the manner in which the blocks are connected in the flow chart. Each block has a reference number assigned to it.

The process starts at start block 298 and then proceeds to the first operation, represented by flow diagram box 300. In this operation, the frequency assigned to one electrode is picked as a starting location corresponding to the first note of a familiar melody. This electrode can be used each time as the spatial or place location of the first note of a song or tune presented. In the next operation, the melody is played to the patient, as represented by flow diagram box 305 in FIG. 14. Initially, the melody is played in an original format without any distortion to the notes of the melody. As mentioned, the tune comprises a series of notes, or tone bursts, each tone burst having a predetermined frequency and duration that is known by a person performing the process. The patient has previously been fitted with a cochlear implant, which processes the received tone bursts and stimulates the cochlea pursuant to programming of the cochlear implant, which programming includes an implant fitting curve (line) that maps the cochlear place or electrode place versus perceived audio frequency, as described above.

The next operation is represented by the decision box 310 in FIG. 14, where the patient determines whether the melody conforms to the melody as remembered by the patient. The melody is deemed to sound "correct" if the melody conforms to the melody as remembered by the patient. If the patient determines that the melody does not sound correct (a "No" output from the decision box 310), then this is an indication that the cochlear implant is mistuned, as the patient is actually hearing a different series of frequencies than those that are actually being delivered to the patient.

In the event that the melody does not sound correct (i.e., it does not conform to the user's memory of the melody), the process then proceeds to the flow diagram box 315, where the notes of the melody are distorted or varied in a predetermined manner in an attempt to make the melody, as presented by the cochlear implant, conform more closely to the patient's memory of the melody. That is, the respective frequency of one or more of the notes in the melody is varied in a predetermined manner with the result being a distorted version of the original melody. The melody (in the distorted format) is then delivered to the patient, as represented by flow diagram box 305. The goal is to distort the melody in such a way that the distorted version of the melody sounds "correct" to the patient. It should be appreciated that the distorted version of the melody will sound awkward or incorrect to an observer that is not fitted with a cochlear implant or to an observer that is fitted with a properly-tuned cochlear implant. The operations of delivering the melody to the patient, distorting the melody, and then receiving feedback from the patient as to whether the distorted melody sounds correct is iteratively repeated until the distorted version of the melody conforms to the patient's memory.

Once the melody has been distorted in a manner such that it conforms to the patient's memory of the melody, the programming of the patient's cochlear implant is then adjusted until the distorted version of the melody sounds incorrect and the original version of the melody sounds correct, as represented by flow diagram box 320 in FIG. 14. The amount of adjustment to the implant is determined based on the amount of frequency distortion that was required to distort the melody so that it conformed to the patient's memory.

There is now described a particular method for distorting the notes of the melody in a predetermined manner pursuant to the operation of flow diagram box 315. As discussed above, it has been discovered empirically, as shown in FIGS. 5A-5C, that the relationship between the cochlear place (mm) versus the Log(perceived audio frequency (Hz)) is approximately linear for a large part of the perceived hearing range. Pursuant to a melody distorting process, each note in the melody is distorted or varied in a predetermined manner as defined by the following equation, which describes the amount of frequency distortion of each note of the melody, with the notes being represented by the Log of their respective frequency. The equation is as follows:

$$\log(F[i]) = \log(fLoc) + k(\log(fNote) - \log(fNote0))$$

where F[i] is the distorted frequency of the melody note that is being distorted, fLoc is a reference frequency that is equal to the frequency assigned to the electrode that was picked as the starting location corresponding to the first note of the melody, fNote is the original frequency of the melody note prior to distortion, fNote0 is the original frequency of the first note of the melody prior to distortion, and k is a variable that is iteratively varied when presenting the melody to the patient. Pursuant to the operation of flow diagram box 315, the foregoing equation is applied to each note in the melody to arrive at a distorted set of notes for the melody. It should be appreciated that the foregoing equation is exemplary and that the notes of the melody can be distorted in other manners.

Further explanation of the equation is now provided. The first portion of the right hand side of the equation is related to fLoc, which is the frequency of a reference electrode to which the melody is tied. The second portion of the right hand side of the equation represents the difference in frequency between the current note, fNote, in the melody and the first note, fNote0, in the melody. If the equation is used to distort the first note of the melody, then fNote=fNote0, such that the frequency of first distorted note in the melody is simply equal to the frequency of the reference electrode, fLoc. Subsequent notes in the melody are distorted by the frequency difference (i.e., (fNote-fNote0)) between the subsequent note and the first note in the melody multiplied by the factor k (which represents a correction factor that is varied) and summed with the frequency of the first electrode, fLoc. Thus, the value of correction factor k dictates the amount of frequency variation between the notes in the distorted melody. As k increases, the frequency variation between notes in the melody also increases, and vice-versa. Note that k is therefore similar to the inverse of the implant fitting slope. As the implant fitting slope increases, the frequency variation as a function of cochlear place decreases and vice-versa.

Thus, in the operation of flow diagram box 315, the notes of the melody can be distorted pursuant to the above equation and the distorted melody presented to the patient in the operation of flow diagram box 305. The distorted melody is presented to the patient with variations of the correction factor k. When the patient listens to the melody as distorted by a new correction factor k, the patient makes the determination as to whether the notes in the melody sound too close together in pitch or whether the notes sound too far apart in pitch. If the notes sound too close together in pitch, then the notes are next distorted using a higher value of correction factor k than previously used, which effectively magnifies the differences in frequency (i.e., log(fNote)-log(fNote0)) between the notes in the melody. The value of correction factor k is iteratively increased or decreased until the melody sounds "correct" to the patient. If, for example, the notes sound too far apart in pitch compared to a previous rendition of the melody, the notes are subsequently distorted with a lower value of correction factor k than previously used, which effectively reduced the differences in frequency between the notes in the melody.

The process of distorting the notes in the melody, presenting the distorted melody to the patient, and subsequently distorting the melody again until the melody sounds correct can be performed using a plurality of reference electrodes as fLoc. For example, the melody can be distorted a first time using the frequency mapped to electrode 1 as fLoc, distorted a second time using the frequency of electrode 2 as fLoc, and so one for various electrodes. This will permit the melody to be presented to the patient at different locations in the electrode array, which corresponds to different cochlear locations.

As mentioned, when the distorted melody sounds "correct" to the patient, this is an indication that the patient's cochlear implant is mistuned. This is because the patient is actually being presented with a distorted version of the melody that actually differs from the original melody. At this stage in the process, pursuant flow diagram box 320, the frequency to electrode mapping of the cochlear implant is adjusted such that the distorted melody sounds awkward or incorrect to the patient and the original melody sounds correct to the patient in that it conforms to the patient's memory.

The electrode mapping can be adjusted by varying the implant fitting line of the cochlear implant by a factor inversely proportional to the correction factor k that was previously found to distort the melody in a manner that made the melody sound correct to the patient. As mentioned, the correction factor k is akin to the inverse of the implant fitting slope.

It should be appreciated that the slope of the implant fitting line does not have to be adjusted uniformly across the entire electrode array. Rather, the slope can be adjusted differently based on different regions of the array. For example, the region of electrodes 1-3 can be adjusted in one manner, the region of electrode 4-6 in another manner, and so on to generate an adjusted frequency-to-electrode map. One additional parameter that can be assigned in the frequency to electrode map is the frequency assigned to the first electrode. One way to assign this frequency is to have the patient listen to familiar voices for variations of frequencies assigned to the initial electrode. The patient can then pick the frequency for which the voices sound most natural. This frequency is then assigned to the first electrode in the array.

A number of embodiments have been described. Nevertheless, it will be understood that various modifications may be made without departing from the spirit and scope of the claims. Accordingly, other embodiments are within the scope of the following claims.

What is claimed is:

1. A method for adjusting a cochlear implant system, the method comprising:
   using an interface of a software program to present variations of a musical melody to a user through a multi-electrode array implanted into the cochlea of the user, wherein the multi-electrode array has an associated implant fitting line that defines a relationship between cochlear places of implant electrodes and associated audio frequencies;
   allowing the user to select at the interface a preferred variation of the musical melody; and
   determining a correct slope of the implant fitting line of the multi-electrode array based on the variation of the musical melody selected by the user.

2. The method of claim 1, wherein presenting variations of the musical melody comprises presenting the musical melody to the user with different slopes of the implant fitting line such that the user perceives different renditions of the musical melody.

3. The method of claim 2, further comprising determining an offset of the implant fitting line relative to an intrinsic fitting line of the user's cochlea, comprising:
   using the interface of the software program to present variations of a familiar sound to the user, the variations achieved by varying the offset of the implant fitting line; and
   allowing the user to select at the interface a variation of the familiar sound at a first offset.

4. The method of claim 3, further comprising using virtual electrodes to deliver stimuli to the cochlear places.

5. The method of claim 4, wherein using the virtual electrodes comprises presenting weighted stimulus currents simultaneously at two electrodes.

6. The method of claim 4, wherein using the virtual electrodes comprises presenting time-multiplexed stimulus currents at two closely spaced electrodes.

7. The method of claim 1, wherein presenting variations of the musical melody comprises varying the frequency of one or more of the notes of the musical melody to present distorted versions of the musical melody to the user.

8. The method of claim 7, wherein the selected variation of the musical melody comprises a distorted version of the musical melody.

9. The method of claim 7, wherein determining the correct slope of the implant fitting line of the multi-electrode array based on the variation of the musical melody selected by the user comprises using differences in relative frequencies between an original version of the musical melody and the selected variation of the musical melody to determine the correct slope.

10. A method for adjusting a cochlear implant system, the method comprising:
   (a) determining a best slope of an implant fitting line of an implanted multi-electrode array in the cochlea of a user, comprising
      using an interface of a software program to present variations of a musical tune to the user by varying the slope of the implant fitting line of the multi-electrode array, wherein the implant fitting line defines a relationship between cochlear places of implant electrodes and associated audio frequencies, and
      allowing the user to select at the interface a variation of the tune presented with a first implant fitting line slope; and
   (b) determining an offset of the implant fitting line relative to an intrinsic fitting line of the user's cochlea, comprising
      using the interface of the software program to present variations of a familiar sound to the user by varying the offset of the implant fitting line of the multi-electrode array, and
      allowing the user to select at the interface a variation of the familiar sound at a first offset.

11. The method of claim 10, wherein the familiar sound presented in step (b) comprises human speech.

12. The method of claim 10, wherein determining the best slope in (a) comprises
   using a converging process wherein further incremental changes to the slope do not yield appreciable perceived improvement in the quality of the musical tune presented, in which event the best slope has been found.

13. The method of claim 10, wherein determining the best slope in (a) comprises
   presenting the first note in different variations of the musical tune (1) at a same electrode without using a virtual electrode or (2) at a same cochlear place using the virtual electrode.

14. The method of claim 10, wherein determining the best slope comprises:
   storing different values of slopes of the implant fitting line in a computer memory; and
   presenting the variations of the musical tune using the different values of the slopes.

15. The method of claim 10, wherein:
   the electrode array is placed in the user's scala tympani; and
   the electrode array includes at least eight electrode contacts with even inter-electrode spacing.

16. The method of claim 10, wherein virtual electrodes are implemented to deliver stimuli to places on the cochlea.

17. The method of claim 16, wherein the virtual electrodes are implemented by presenting weighted stimulus currents simultaneously at two electrodes.

18. The method of claim 16, wherein the virtual electrodes are implemented by presenting time-multiplexed stimulus currents at two closely spaced electrodes.

19. A method for finding the slope of an implant fitting line, the method comprising:
   determining the slope of an implant fitting line of a multi-electrode array implanted in the cochlea of a user, comprising
      using an interface of a software program to present variations of a musical tune to the user with a different slope of the implant fitting line at each presentation through the multi-electrode array, and
      allowing the user to select at the interface a variation of the musical tune with a first slope, wherein the implant fitting line defines a relationship between cochlear places of implant electrodes and associated audio frequencies.

20. The method of claim 19, wherein
presenting the variations of the musical tune comprises incrementally changing the slope of the implant fitting line until further incremental changes to the slope do not yield appreciable improvement in the quality of the tune, in which event the best slope has been found.

21. The method of claim 19, wherein virtual electrodes are implemented to deliver stimuli to places on the cochlea.

22. A method for fitting a cochlear implant system, the method comprising:
using an interface of a software program to present a first musical melody to a user through a multi-electrode array of a cochlear implant system implanted in the cochlea of the user, the first musical melody comprising a series of notes, each note having a predetermined frequency;
using the interface to present a second musical melody to the user, wherein the second musical melody varies the frequency of one or more of the notes of the first melody in a predetermined manner such that the second musical melody comprises a distorted version of the first musical melody;
receiving at the interface a user selection of one of the first musical melody and the second musical melody as preferable to the user; and
adjusting an implant fitting line of the multi-electrode array based on the user selection, wherein the implant fitting line defines a relationship between cochlear places of implant electrodes and associated audio frequencies.

23. The method of claim 22, wherein:
the first musical melody comprises an original version of a well-known melody; and
the second musical melody comprises a distorted version of the well-known melody.

24. The method of claim 23, wherein adjusting the implant fitting line comprising causing the first musical melody to conform to the musical melody as remembered by the user.

25. The method of claim 22, wherein varying the frequency of the one or more of the notes of the first melody comprises:
assigning the frequency of a first note of the first melody to a predetermined electrode of the array; and
varying the frequencies of subsequent notes in the first melody relative to the assigned frequency.

26. The method of claim 22, wherein varying the frequency of the one or more of the notes of the first melody comprises:
for all notes in the first musical melody, calculating a difference in frequency relative to the first note;
multiplying the difference by a correction factor; and
adding the product of the difference and the correction factor to the frequency of the first note to arrive at the second musical melody.

27. The method of claim 26, wherein the correction factor represents the variation between the first musical melody and the second musical melody.

28. The method of claim 26, further comprising:
varying the correction factor to achieve additional distorted versions of the first musical melody; and
using the interface to present the additional distorted versions of the first musical melody to the user.

29. The method of claim 22, further comprising varying an association between the one or more of the notes of the first melody and various electrodes in the array, wherein the implant fitting line is adjusted differently based on a location of the various electrodes along the electrode array.

30. A method for adjusting a cochlear implant system, the method comprising:
using an interface of a software program to present variations of a musical melody to a user through an implanted multi-electrode array, the multi-electrode array having an associated implant fitting line that defines a relationship between cochlear places of implant electrodes and associated audio frequencies, wherein presenting the variations comprises varying the frequency of one or more of the notes of the musical melody to present a distorted version of the musical melody to the user;
allowing the user to select at the interface a variation of the musical melody that most closely conforms to the musical melody as remembered by the user, wherein the variation of the musical melody that most closely conforms to the musical melody as remembered by the user comprises a distorted version of the musical melody; and
determining a correct slope of the implant fitting line of the multi-electrode array based on the variation of the musical melody selected by the user.

31. A method for adjusting a cochlear implant system, the method comprising:
using an interface of a software program to present variations of a musical melody to a user through an implanted multi-electrode array, the multi-electrode array having an associated implant fitting line that defines a relationship between cochlear places of implant electrodes and associated audio frequencies, wherein presenting the variations comprises varying the frequency of one or more of the notes of the musical melody to present a distorted version of the musical melody to the user;
allowing the user to select at the interface a variation of the musical melody that most closely conforms to the musical melody as remembered by the user; and
determining a correct slope of the implant fitting line of the multi-electrode array based on the variation of the musical melody selected by the user using differences in relative frequencies between an original version of the musical melody and the selected variation of the musical melody to determine the correct slope.

* * * * *